United States Patent
Hoelzemann et al.

(10) Patent No.: US 8,202,882 B2
(45) Date of Patent: Jun. 19, 2012

(54) 5-CYANOTHIENOPYRIDINES FOR THE TREATMENT OF TUMOURS

(75) Inventors: Guenter Hoelzemann, Seeheim-Jugenheim (DE); Ulrich Graedler, Heidelberg (DE); Hartmut Greiner, Weiterstadt (DE); Christiane Amendt, Muehltal/Trautheim (DE); Djordje Musil, Seeheim-Jugenheim (DE); Per Hillertz, Gothenburg (SE)

(73) Assignee: Merck Patent Gesellschaft MIT Beschränkter Haftung, Darmstadt (DE)

( * ) Notice: Subject to any disclaimer, the term of this patent is extended or adjusted under 35 U.S.C. 154(b) by 0 days.

(21) Appl. No.: 12/738,158

(22) PCT Filed: Sep. 19, 2008

(86) PCT No.: PCT/EP2008/007888
§ 371 (c)(1),
(2), (4) Date: Apr. 15, 2010

(87) PCT Pub. No.: WO2009/049743
PCT Pub. Date: Apr. 23, 2009

(65) Prior Publication Data
US 2010/0234369 A1     Sep. 16, 2010

(30) Foreign Application Priority Data
Oct. 16, 2007   (DE) .......................... 10 2007 049 451

(51) Int. Cl.
*A61K 31/4365* (2006.01)
*C07D 495/04* (2006.01)
*C07D 401/14* (2006.01)

(52) U.S. Cl. ........................................ 514/301; 546/114
(58) Field of Classification Search .................. 514/301; 546/114
See application file for complete search history.

(56) References Cited

U.S. PATENT DOCUMENTS
2007/0213328 A1   9/2007   Drysdale et al.

FOREIGN PATENT DOCUMENTS
| WO | WO 2005/034950 A1 | 4/2005 |
| WO | WO 2005/058315 A1 | 6/2005 |
| WO | WO 2006/125531 A2 | 11/2006 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Golub et al. Science (1999), vol. 286 531-537.*
Lala et al. Cancer and Metastasis Reviews (1998), 17(1), 91-106.*
"HIV-AIDS." Mayoclinic. URL: http://www.mayoclinic.com/health/hiv-aids/DS00005/DSECTION=treatments-and-drugs Apr. 11, 2010.*
"Alzheimers." (URL: <http://www.cnn.com/Health/mentalhealth/alzheimers/#>) Apr. 11, 2010.*
International Search Report of PCT/EP2008/007888 (Jan. 30, 2009).

* cited by examiner

*Primary Examiner* — Rebecca Anderson
*Assistant Examiner* — Samantha Shterengarts
(74) *Attorney, Agent, or Firm* — Millen, White, Zelano & Branigan, P.C.

(57) ABSTRACT

Novel 5-cyanothienopyridines of the formula (I), in which $R^1$, $R^2$ and $R^3$ have the meanings indicated in claim 1, are inhibitors of TGF-beta receptor kinase, and can be employed, inter alia, for the treatment of tumors.

11 Claims, No Drawings

5-CYANOTHIENOPYRIDINES FOR THE TREATMENT OF TUMOURS

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular TGF-beta receptor kinases, plays a role, furthermore to pharmaceutical compositions which comprise these compounds, and to the use of the compounds for the treatment of kinase-induced diseases.

Transforming growth factor beta is the prototype of the TGF-beta super-family, a family of highly preserved, pleiotropic growth factors, which carry out important functions both during embryo development and also in the adult organism. In mammals, three isoforms of TGF-beta (TGF-beta 1, 2 and 3) have been identified, TGF-beta 1 being the commonest isoform (Kingsley (1994) Genes Dev 8:133-146). TGF-beta 3 is expressed, for example, only in mesenchymal cells, whereas TGF-beta 1 is found in mesenchymal and epithelial cells. TGF-beta is synthesised, as pre-proprotein and is released in inactive form into the extracellular matrix (Derynck (1985) Nature 316: 701-705; Bottinger (1996) PNAS 93: 5877-5882). Besides the proregion cleaved off, which is also known as latency associated peptide (LAP) and remains associated with the mature region, one of the 4 isoforms of the latent TGF-beta binding proteins (LTBP 1-4) may also be bonded to TGF-beta (Gentry (1988) Mol Cell Biol 8: 4162-4168, Munger (1997) Kindey Int 51: 1376-1382). The activation of the inactive complex that is necessary for the development of the biological action of TGF-beta has not yet been clarified in full. However, proteolytic processing, for example by plasmin, plasma transglutaminase or thrombospondin, is certainly necessary (Munger (1997) Kindey Int 51: 1376-1382). The activated ligand TGF-beta mediates its biological action via three TGF-beta receptors on the membrane, the ubiquitously expressed type I and type II receptors and the type III receptors betaglycan and endoglin, the latter only being expressed in endothelial cells (Gougos (1990) J Biol Chem 264: 8361-8364, Loeps-Casillas (1994) J Cell Biol 124:557-568). Both type III TGF-beta receptors lack an intracellular kinase domain which facilitates signal transmission into the cell. Since the type III TGF-beta receptors bind all three TGF-beta isoforms with high affinity and type II TGF-beta receptor also has higher affinity for ligands bonded to type III receptor, the biological function is thought to consist in regulation of the availability of the ligands for type I and type II TGF-beta receptors (Lastres (1996) J Cell Biol 133:1109-1121; Lopes-Casillas (1993) Cell 73: 1435-1344). The structurally closely related type I and type II receptors have a serine/threonine kinase domain, which is responsible for signal transmission, in the cytoplasmatic region. Type II TGF-beta receptor binds TGF-beta, after which the type I TGF-beta receptor is recruited to this signal-transmitting complex. The serine/threonine kinase domain of the type II receptor is constitutively active and is able to phosphorylate seryl radicals in this complex in the so-called GS domain of the type I receptor. This phosphorylation activates the kinase of the type I receptor, which is now itself able to phosphorylate intracellular signal mediators, the SMAD proteins, and thus initiates intracellular signal transmission (summarised in Derynck (1997) Biochim Biophys Acta 1333: F105-F150).

The proteins of the SMAD family serve as substrates for all TGF-beta family receptor kinases. To date, 8 SMAD proteins have been identified, which are divided into 3 groups: (1) receptor-associated SMADs (R-SMADs) are direct substrates of the TGF-β receptor kinases (SMAD1, 2, 3, 5, 8); (2) co-SMADs, which associate with the R-Smads during the signal cascade (SMAD4); and (3) inhibitory SMADs (SMAD6, 7), which inhibit the activity of the above-mentioned SMAD proteins. Of the various R-SMADs, SMAD2 and SMAD3 are the TGF-beta-specific signal mediators. In the TGF-beta signal cascade, SMAD2/SMAD3 are thus phosphorylated by the type I TGF-beta receptor, enabling them to associate with SMAD4. The resultant complex of SMAD2/SMAD3 and SMAD4 can now be translocated into the cell nucleus, where it can initiate the transcription of the TGF-beta-regulated genes directly or via other proteins (summarised in Itoh (2000) Eur J Biochem 267: 6954-6967; Shi (2003) Cell 113: 685-700).

The spectrum of the functions of TGF-beta is wide-ranging and dependent on cell type and differentiation status (Roberts (1990) Handbook of Experimental Pharmacology: 419-472). The cellular functions which are influenced by TGF-beta include: apoptosis, proliferation, differentiation, mobility and cell adhesion. Accordingly, TGF-beta plays an important role in a very wide variety of biological processes. During embryo development, it is expressed at sites of morphogenesis and in particular in areas with epithelial-mesenchymal interaction, where it induces important differentiation processes (Pelton (1991) J Cell Biol 115:1091-1105). TGF-beta also carries out a key function in the self-renewal and maintenance of an undifferentiated state of stem cells (Mishra (2005) Science 310: 68-71). In addition, TGF-beta also fulfils important functions in the regulation of the immune system. It generally has an immunosuppressive action, since it inhibits, inter alia, the proliferation of lymphocytes and restricts the activity of tissue macrophages. TGF-beta thus allows inflammatory reactions to subside again and thus helps to prevent excessive immune reactions (Bogdan (1993) Ann NY Acad Sci 685: 713-739, summarised in Letterio (1998) Annu Rev Immunol 16: 137-161). Another function of TGF-beta is regulation of cell proliferation. TGF-beta inhibits the growth of cells of endothelial, epithelial and haematopoietic origin, but promotes the growth of cells of mesenchymal origin (Tucker (1984) Science 226:705-707, Shipley (1986) Cancer Res 46:2068-2071, Shipley (1985) PNAS 82: 4147-4151). A further important function of TGF-beta is regulation of cellular adhesion and cell-cell interactions. TGF-beta promotes the build-up of the extracellular matrix by induction of proteins of the extracellular matrix, such as, for example, fibronectin and collagen. In addition, TGF-beta reduces the expression of matrix-degrading metalloproteases and inhibitors of metalloproteases (Roberts (1990) Ann NY Acad Sci 580: 225-232; Ignotz (1986) J Biol Chem 261: 4337-4345; Overall (1989) J Biol Chem 264: 1860-1869); Edwards (1987) EMBO J. 6: 1899-1904).

The broad spectrum of action of TGF-beta implies that TGF-beta plays an important role in many physiological situations, such as wound healing, and in pathological processes, such as cancer and fibrosis.

TGF-beta is one of the key growth factors in wound healing (summarised in O'Kane (1997) Int J Biochem Cell Biol 29: 79-89). During the granulation phase, TGF-beta is released from blood platelets at the site of injury. TGF-beta then regulates its own production in macrophages and induces the secretion of other growth factors, for example by monocytes. The most important functions during wound healing include stimulation of chemotaxis of inflammatory cells, the synthesis of extracellular matrix and regulation of the proliferation, differentiation and gene expression of all important cell types involved in the wound-healing process.

Under pathological conditions, these TGF-beta-mediated effects, in particular the regulation of the production of extracellular matrix (ECM), can result in fibrosis or scars in the skin (Border (1994) N Engl J Med 331:1286-1292).

For the fibrotic diseases, diabetic nephropathy and glomeronephritis, it has been shown that TGF-beta promotes renal cell hypertrophy and pathogenic accumulation of the extracellular matrix. Interruption of the TGF-beta signalling pathway by treatment with anti-TGF-beta antibodies prevents expansion of the mesangial matrix, progressive reduction in kidney function and reduces established lesions of diabetic glomerulopathy in diabetic animals (Border (1990) 346: 371-374, Yu (2004) Kindney Int 66: 1774-1784, Fukasawah (2004) Kindney Int 65: 63-74, Sharma (1996) Diabetes 45: 522-530).

TGF-beta also plays an important role in liver fibrosis. The activation, essential for the development of liver fibrosis, of the hepatic stellate cells to give myofibroblasts, the main producer of the extracellular matrix in the course of the development of liver cirrhosis, is stimulated by TGF-beta. It has likewise been shown here that interruption of the TGF-beta signalling pathway reduces fibrosis in experimental models (Yata (2002) Hepatology 35:1022-1030; Arias (2003) BMC Gastroenterol 3:29) TGF-beta also takes on a key function in the formation of cancer (summarised in Derynck (2001) Nature Genetics: 29: 117-129; Elliott (2005) J Clin One 23: 2078-2093). In early stages of the development of cancer, TGF-beta counters the formation of cancer. This tumour-suppressive action is based principally on the ability of TGF-beta to inhibit the division of epithelial cells. By contrast, TGF-beta promotes cancer growth and the formation of metastases in late tumour stages. This can be attributed to the fact that most epithelial tumours develop a resistance to the growth-inhibiting action of TGF-beta, and TGF-beta simultaneously supports the growth of the cancer cells via other mechanisms. These mechanisms include promotion of angiogenesis, the immunosuppressive action, which supports tumour cells in avoiding the control function of the immune system (immunosurveillance), and promotion of invasiveness and the formation of metastases. The formation of an invasive phenotype of the tumour cells is a principal prerequisite for the formation of metastases. TGF-beta promotes this process through its ability to regulate cellular adhesion, motility and the formation of the extracellular matrix. Furthermore, TGF-beta induces the transition from an epithelial phenotype of the cell to the invasive mesenchymal phenotype (epithelial mesenchymal transition=EMT). The important role played by TGF-beta in the promotion of cancer growth is also demonstrated by investigations which show a correlation between strong TGF-beta expression and a poor prognosis. Increased TGF-beta level have been found, inter alia, in patients with prostate, breast; intestinal and lung cancer (Wikström (1998) Prostate 37: 19-29; Hasegawa (2001) Cancer 91: 964-971; Friedman (1995), Cancer Epidemiol Biomarkers Prev. 4:549-54).

Owing to the cancer-promoting actions of TGF-beta described above, inhibition of the TGF-beta signalling pathway, for example via inhibition of the TGF-beta type I receptor, is a possible therapeutic concept. It has been shown in numerous preclinical trials that interruption of the TGF-beta signalling pathway does indeed inhibit cancer growth. Thus, treatment with soluble TGF-beta type II receptor reduces the formation of metastases in transgenic mice, which develop invasive breast cancer in the course of time (Muraoka (2002) J Clin Invest 109: 1551-1559, Yang (2002) J Olin Invest 109: 1607-1615).

Tumour cell lines which express a defective TGF-beta type II receptor exhibit reduced tumour and metastatic growth (Oft (1998) Curr Biol 8: 1243-1252, McEachern (2001) Int J Cancer 91:76-82, Yin (1999) J Clin Invest 103: 197-206).

Conditions "characterised by increased TGF-β activity" include those in which TGF-β synthesis is stimulated so that TGF-β is present at increased levels or in which latent TGF-β protein is undesirably activated or converted to active TGF-β protein or in which TGF-β receptors are upregulated or in which the TGF-β protein shows enhanced binding to cells or the extracellular matrix in the location of the disease. Thus, in each case "increased activity" refers to any condition in which the biological activity of TGF-β is undesirably high, regardless of the cause.

A number of diseases have been associated with TGF-β1 overproduction.

Inhibitors of the intracellular TGF-β signalling pathway are suitable treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, sclerodermatitis, dermatomyositis, eosinophilic fasciitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and sclerodermatitis, chemical contact or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post-glaucoma drainage surgery and are associated with TGF-β1 overproduction.

Fibrotic diseases associated with TGF-β1 overproduction can be divided into chronic conditions, such as fibrosis of the kidney, lung and liver, and more acute conditions, such as dermal scarring and restenosis (Chamberlain, J. Cardiovascular Drug Reviews, 19(4): 329-344). Synthesis and secretion of TGF-β1 by tumour cells can also lead to immune suppression, as seen in patients with aggressive brain or breast tumours (Arteaga, et al. (1993) J. Clin. Invest. 92: 2569-2576). The course of leishmanial infection in mice is drastically altered by TGF-β1 (Barral-Netto, et al. (1992) Science 257: 545-547). TGF-β1 exacerbated the disease, whereas TGF-β1 antibodies halted the progression of the disease in genetically susceptible mice. Genetically resistant mice became susceptible to leishmanial infection upon administration of TGF-β1.

The profound effects on extracellular matrix deposition have been reviewed (Rocco and Ziyadeh (1991) in Contemporary Issues in Nephrology v. 23, Hormones, autocoids and the kidney. ed. Jay Stein, Churchill Livingston, N.Y. pp. 391-410; Roberts, et al. (1988) Rec. Prog. Hormone Res. 44: 157-197) and include stimulation of the synthesis and inhibition of the degradation of extracellular matrix components. Since the structural and filtration properties of the glomerulus are largely determined by the extracellular matrix composition of the mesangium and glomerular membrane, it is not surprising that TGF-β1 has profound effects on the kidney. The accumulation of mesangial matrix in proliferative glomerulonephritis (Border, et al., (1990) Kidney Int. 37: 689-695) and diabetic nephropathy (Mauer, et al. (1984) J. Clin. Invest. 74: 1143-1155) are clear and dominant pathological features of the diseases. TGF-β1 levels are elevated in human diabetic glomerulosclerosis (advanced neuropathy) (Yamamoto, et al. (1993) Proc. Natl. Acad. Sci. 90: 1814-1818). TGF431 is an important mediator in the genesis of renal fibrosis in a number of animag models (Phan, et al. (1990) Kidney Int. 37: 426; Okuda, et al. (1990) J. Clin. Invest. 86: 453). Suppression of experimentally induced glomerulonephritis in rats has been demonstrated by antiserum against TGF-β1 (Border, et al. (1990) Nature 346: 371) and by an extracellular matrix protein, decorin, which can bind TGF-β1 (Border, et al. (1992) Nature 360: 361-363).

Excessive TGF-β1 leads to dermal scar-tissue formation. Neutralising TGF-β1 antibodies injected into the margins of healing wounds in rats has been shown to inhibit scarring without interfering with the rate of wound healing or the tensile strength of the wound (Shah, et al. (1992) Lancet 339: 213-214). At the same time there was reduced angiogenesis, a reduced number of macrophages and monocytes in the wound, and a reduced amount of disorganised collagen fibre deposition in the scar tissue.

TGF-β1 may be a factor in the progressive thickening of the arterial wall which results from the proliferation of smooth muscle cells and deposition of extracellular matrix in the artery after balloon angioplasty. The diameter of the restenosed artery may be reduced by 90% by this thickening, and since most of the reduction in diameter is due to extracellular matrix rather than smooth muscle cell bodies, it may be possible to reopen these vessels to 50% simply by reducing excessive extracellular matrix deposition. In undamaged pig arteries transfected in vivo with a TGF-β1 gene, TGF-β1 gene expression was associated with both extracellular matrix synthesis and hyperplasia (Nabel, et al. (1993) Proc. Natl. Acad. Sci. USA 90: 10759-10763). The TGF-β1-induced hyperplasia was not as extensive as that induced with PDGF-BB, but the extracellular matrix was more extensive with TGF-β1 transfectants. No extracellular matrix deposition was associated with hyperplasia induced by FGF-1 (a secreted form of FGF) in this gene transfer pig model (Nabel (1993) Nature 362: 844-846).

There are various types of cancer where TGF-β1 produced by the tumour may be deleterious. MATLyLu rat prostate cancer cells (Steiner and Barrack (1992) Mol. Endocrinol. 6: 15-25) and MCF-7 human breast cancer cells (Arteaga, et al. (1993) Cell Growth and Differ. 4: 193-201) became more tumorigenic and metastatic after transfection with a vector expressing the mouse TGF-β1. TGF-β1 has been associated with angiogenesis, metastasis and poor prognosis in human prostate and advanced intestinal cancer (Wikstrom, P., et al. (1988) Prostate 37; 19-29; Saito, H., et al. (1999) Cancer 86: 1455-1462). In breast cancer, a poor prognosis is associated with elevated TGF-β (Dickson, et al. (1987) Proc. Natl. Acad. Sci. USA 84: 837-841; Kasid, et al. (1987) Cancer Res. 47: 5733-5738; Daly, et al. (1990) J. Cell Biochem. 43: 199-211; Barrett-Lee, et al. (1990) Br. J. Cancer 61: 612-617; King, et al (1989) J. Steroid Biochem. 34: 133-138; Welch, et al (1990) Proc. Natl. Acad. Sci USA 87: 7678-7682; Walker et al. (1992) Eur. J. Cancer 238: 641-644), and induction of TGF-β1 by tamoxifen treatment (Butta, et al. (1992) Cancer Res. 52: 4261-4264) has been associated with failure of tamoxifen treatment for breast cancer (Thompson, et al. (1991) Br. J. Cancer 63: 609-614). Anti-TGF-β1 antibodies inhibit the growth of MDA-231 human breast cancer cells in athymic mice (Arteaga, et al. (1993) J. Clin. Invest. 92: 2569-2576), a treatment which is correlated with an increase in natural killer cell activity in the spleen. CHO cells transfected with latent TGF-β1 also showed decreased NK activity and increased tumour growth in nude mice (Wallick, et al. (1990) J. Exp. Med. 172: 177-1784). Thus, TGF-β secreted by breast tumours may cause endocrine immune suppression. High plasma concentrations of TGF-β1 show a poor prognosis for advanced breast cancer patients (Anscher, et al. (1993) N. Engl. J. Med. 328: 1592-1598). Patients with high circulating TGF-β before high dose chemotherapy and autologous bone marrow transplantation are at high risk of a hepatic veno-occlusive disease (15-50% of all patients with a mortality rate up to 50%) and idiopathic interstitial pneumonitis (40 to 60% of all patients). The implication of these findings is 1) that elevated plasma levels of TGF-β1 can be used to identify at-risk patients and 2) that reduction of TGF-β1 can decrease the morbidity and mortality of these common treatments for breast cancer patients.

Many malignant cells secrete transforming growth factor β (TGF-β), a potent immunosuppressant, suggesting that TGF-β production may represent a significant tumour escape mechanism from host immunosurveillance. Establishment of a leukocyte sub-population with a disrupted TGF-β signalling pathway in the tumour-bearing host offers a powerful measure for immunotherapy of cancer. A transgenic animal model with a disrupted TGF-β signalling pathway in T cells is capable of eradicating a normally lethal TGF-β-overexpressing lymphoma tumour, EL4 (Gorelik and Flavell, (2001) Nature Medicine 7 (10): 1118-1122). Downregulation of TGF-β secretion in tumour cells results in restoration of immunogenicity in the host, while T-cell insensitivity to TGF-β results in accelerated differentiation and autoimmunity, elements of which may be required in order to combat self-antigen-expressing tumours in a tolerised host. The immunosuppressive effects of TGF-β have also been implicated in a sub-population of HIV patients with lower than predicted immune response based on their CD4/CD8 T cell counts (Garba, et al., J. Immunology (2002) 168: 2247-2254). A TGF-β-neutralising antibody was capable of reversing the effect in culture, indicating that TGF-β signalling pathway inhibitors may be suitable in reversing the immune suppression present in this subset of HIV patients.

During the earliest stages of carcinogenesis, TGF-β1 can act as a potent tumour suppressor and may mediate the actions of some chemopreventive agents. At a certain point during the development and progression of malignant neoplasms, tumour cells appear to escape from TGF-β-dependent growth inhibition in parallel with the appearance of biologically active TGF-β in the microenvironment. The dual tumour suppression/tumour promotion roles of TGF-β have been most clearly elucidated in a trans-genic system overexpressing TGF-β in keratinocytes. While the transgenics were more resistant to formation of benign skin lesions, the rate of metastatic conversion in the transgenics was dramatically increased (Cui, et al, (1996) Cell 86(4): 531-42). The production of TGF-β1 by malignant cells in primary tumours appears to increase with advancing stages of tumour progression. Studies in many of the major epithelial cancers suggest that the increased production of TGF-β by human cancers occurs as a relatively late event during tumour progression. Furthermore, this tumour-associated TGF-β provides the tumour cells with a selective advantage and promotes tumour progression. The effects of TGF-β on cell-cell and cell-stroma interactions results in a greater propensity for invasion and metastasis. Tumour-associated TGF-β may allow tumour cells to escape from immunosurveillance since it is a potent inhibitor of the clonal expansion of activated lymphocytes. TGF-β has also been shown to inhibit the production of angiostatin. Cancer therapeutic modalities, such as radiation therapy and chemotherapy, induce the production of activated TGF-β in the tumour, thereby selecting outgrowth of malignant cells that are resistant to TGF-β growth inhibitory effects. Thus, these anticancer treatments increase the risk and hasten the development of tumours with enhanced growth and invasiveness. In this situation, agents targeting TGF-β-mediated signal transduction might be a very effective therapeutic strategy. The resistance of tumour cells to TGF-β has been shown to negate many of the cytotoxic effects of radiation therapy and chemotherapy, and the treatment-dependent activation of TGF-β in the stroma may even be detrimental as it makes the microenvironment more conducive to tumour progression and contributes to tissue damage leading to fibrosis. The development of TGF-β signal transduction inhibitors is likely to benefit the treatment of advanced cancer alone and in combination with other therapies.

The compounds are suitable for the treatment of cancer and other conditions influenced by TGF-β by inhibiting TGF-β in a patient in need thereof by administration of the compound(s) to the patient. TGF-β is also suitable against atherosclerotic (T. A. McCaffrey: TGF-βs and TGF-β Receptors in Atherosclerosis: Cytokine and Growth Factor Reviews 2000, 11, 103-114) and Alzheimer's diseases (Masliah, E.; Ho, G.; Wyss-Coray, T.: Functional Role of TGF-β in Alzheimer's Disease Microvascular Injury: Lessons from Transgenic Mice Neurochemistry International 2001, 39, 393-400).

It has been found that the compounds according to the invention and salts thereof have very valuable pharmacological properties while being well tolerated.

In particular, they exhibit TGFβ receptor I kinase-inhibiting properties.

The compounds according to the invention preferably exhibit an advantageous biological activity, which can easily be demonstrated in enzyme-based assays, for example assays as described herein. In such enzyme-based assays, the compounds according to the invention preferably exhibit and cause an inhibiting effect, which is usually documented by $IC_{50}$ values in a suitable range, preferably in the micromolar range and more preferably in the nanomolar range.

As discussed herein, these signalling pathways are relevant for various diseases. Accordingly, the compounds according to the invention are useful in the prophylaxis and/or treatment of diseases that are dependent on the said signalling pathways by interaction with one or more of the said signalling pathways.

The present invention therefore relates to compounds according to the invention as promoters or inhibitors, preferably as inhibitors, of the signalling pathways described herein. The invention therefore preferably relates to compounds according to the invention as promoters or inhibitors, preferably as inhibitors, of the TGFβ signalling pathway.

The present invention furthermore relates to the use of one or more compounds according to the invention in the treatment and/or prophylaxis of diseases, preferably the diseases described herein, that are caused, mediated and/or propagated by an increased TGFβ activity.

The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases as well as to a method for the treatment of the said diseases comprising the administration of one or more compounds according to the invention to a patient in need of such an administration.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in-vitro testing. Typically, a culture of the cell is combined with a compound according to the invention at various concentrations for a period of time which is sufficient to allow the active agents to induce cell death or to inhibit migration, usually between about one hour and one week. In-vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In the scintillation proximity assay (Sorg et al., J. of. Biomolecular Screening, 2002, 7, 11-19) and the flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J., just about to be published, manuscript BJ20020786).

PRIOR ART

5-Cyanothienopyridines which are substituted in the 4-position by a phenyl ring are known from WO 2006/125531 A2.

WO 2005/034950 A1 describes further 5-cyanothienopyridines which act as inhibitors of HSP90 (heat shock protein 90).

WO 2005/058315 A1 describes the use of 5-cyanothienopyridines for the treatment of hepatitis B.

SUMMARY OF THE INVENTION

The invention relates to compounds of the formula I

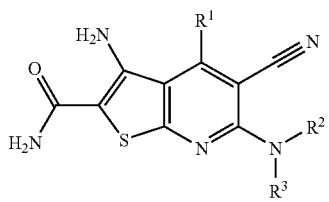

in which
$R^1$ denotes Het
$R^2$, $R^3$ each, independently of one another, denote H, A, AlkNH$_2$, AlkNHA, AlkNAA', AlkNHSO$_2$A, AlkOH, AlkOA, AlkCyc, AlkCycAlkOH, AlkCycAlkOA, AlkCycAlkCOOA, AlkCycAlkCOOH, AlkHet$^1$, AlkOAlkOH, AlkOAlkOA, AlkOAlkNH$_2$, AlkOAlkNHA, AlkOAlkNAA', AlkCHOH(CH$_2$)$_n$OH, AlkO(CH$_2$)$_m$Het$^1$ or AlkAr, where one of the substituents $R^2$ and $R^3$ is ≠H,
$R^2$ and $R^3$ together may also be an alkylene chain having 1 to 6 C atoms, in which one or two non-adjacent CH$_2$ groups may be replaced by N and/or O atoms and/or in which 1 to 6H atoms may be replaced by A, OH, OA, (CH$_2$)$_n$Het$^1$, SO$_2$A and/or Hal,
Alk denotes alkylene having 1 to 6 C atoms, in which 1 to 4H atoms may be replaced by F, Cl and/or Br,
Cyc denotes cycloalkyl having 3 to 7 C atoms, in which 1 to 4H atoms may be replaced by A, Hal, OH and/or OA,
Het denotes a mono- or bicyclic unsaturated and/or aromatic heterocycle having 1 to 4 N, O and/or S atoms, which may be mono-, di- or trisubstituted by A, Hal and/or Ar,
Het$^1$ denotes a monocyclic saturated, unsaturated or aromatic heterocycle having 1 to 4 N, O and/or S atoms, which may be mono-, di- or trisubstituted by A, OH, OA, Hal, SO$_2$A and/or =O (carbonyl oxygen),
Ar denotes phenyl which is unsubstituted or mono-, di- or trisubstituted by A, OH, OA, Hal, SO$_2$NH$_2$, SO$_2$NA and/or SO$_2$NAA',
A, A' each, independently of one another, denote unbranched or branched alkyl having 1-10 C atoms, in which 1-5H atoms may be replaced by F, Cl and/or Br,
Hal denotes F, Cl, Br or I,
m denotes 1, 2, 3, 4,
n denotes 0, 1, 2, 3, 4,
and pharmaceutically usable derivatives, salts, solvates, tautomers and stereoisomers thereof, including mixtures thereof in all ratios.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alkoxides.

Pharmaceutically usable derivatives are taken to mean, for example, the salts of the compounds according to the invention and also so-called prodrug compounds.

Prodrug derivatives are taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, complaint or disorder.

The expression "therapeutically effective amount" also encompasses the amounts which are effective for increasing normal physiological function.

The invention also relates to mixtures of the compounds according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to Claims 1 to 7 and pharmaceutically usable derivatives, solvates, salts, tautomers and stereoisomers thereof, characterised in that
a) for the preparation of a compound of the formula I in which $R^2$, $R^3$=H,
a compound of the formula II

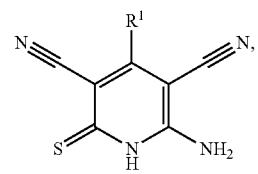

in which $R^1$ has the meaning indicated in Claim 1,
is reacted with a compound of the formula III

$$H_2N\text{---}CO\text{---}CH_2\text{---}Z \qquad III$$

in which
Z denotes Cl, Br, I or a free or reactive functionally modified OH group,
to give a compound of the formula IV

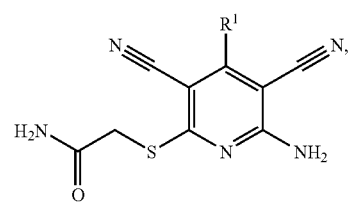

in which $R^1$ has the meaning indicated in Claim 1,
and the resultant compound of the formula IV is subsequently cyclised to give the compound of the formula I, or
b) for the preparation of the compound of the formula I in which at least one of the two radicals $R^2$, $R^3$ is ≠H,
the free amino group in a compound of the formula IV is replaced by Hal, giving a compound of the formula V

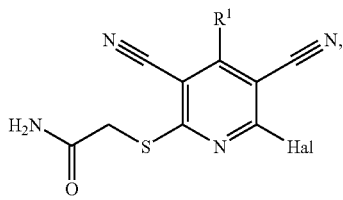

in which R¹ has the meaning indicated in Claim 1,
the compound of the formula V is reacted with a compound of the formula VI

in which R² and R³ have the meanings indicated in claim 1, but at least one of the two radicals R², R³ is ≠H,
to give a compound of the formula VII

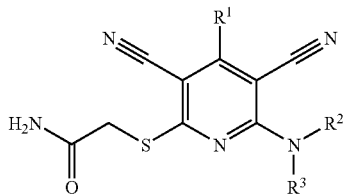

in which R¹, R², R³ have the meanings indicated in claim 1, but at least one of the two radicals R², R³ is ≠H,
and the resultant compound of the formula VII is subsequently cyclised to give the compound of the formula I, and/or c) a base or acid of the formula I is converted into one of its salts.

The invention also relates to the hydrates and solvates of these compounds. Solvates of the compounds are taken to mean adductions of inert solvent molecules onto the compounds, which form owing to their mutual force of attraction. Solvates are, for example, mono- or dihydrates or alcoholates.

The compounds of the formula I according to the invention can also exist in tautomeric forms. Formula I encompasses all these tautomeric forms.

Pharmaceutically usable derivatives are taken to mean, for example, the salts of the compounds according to the invention and also so-called prodrug compounds.

Prodrug derivatives are taken to mean compounds of the formula I which have been modified with, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, complaint or disorder.

The expression "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, their meanings are independent of one another.

Above and below, the radicals R¹, R² and R³ have the meanings indicated for the formula I, unless expressly indicated otherwise.

A A' denote, independently of one another, alkyl, is unbranched (linear) or branched, and has 1, 2, 3, 4, 5, 6, 7, 8, 9 or 10 C atoms. A particularly preferably denotes methyl, ethyl, propyl, isopropyl, butyl, isobutyl, sec-butyl or tent-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl, furthermore also fluoromethyl, difluoromethyl or bromomethyl. Independently of further substitutions, Cyc is cycloalkyl and preferably denotes cyclopropyl, cyclobutyl, cylopentyl, cyclohexyl or cycloheptyl, in particular cyclopropyl and cyclobutyl.

Alk denotes $C_1$-$C_{10}$ alkylene, preferably methylene, ethylene, propylene, butylene, pentylene, hexylene, heptylene, octylene, nonylene or decylene, isopropylene, isobutylene, sec-butylene, 1-, 2- or 3-methylbutylene, 1,1-,1,2- or 2,2-dimethylpropylene, 1-ethylpropylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene. Preference is given to $C_1$-$C_6$ alkylene, particularly preferably methylene, ethylene, propylene, butylene, pentylene or hexylene.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methylsulfonamido)phenyl, o-, m- or p-(N,N-dimethylsulfonamido)phenyl, o-, m- or p-(N-ethyl-N-methylsulfonamido)phenyl, o-, m- or p-(N,N-diethyl-sulfonamido) phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Ar preferably denotes phenyl which is unsubstituted or mono-, di- or trisubstituted by A, OH, OA, Hal, $SO_2NH_2$, $SO_2NA$ and/or $SO_2NAA'$. Ar is particularly preferably phenyl which is monosubstituted by $SO_2NH_2$, $SO_2NA$ or $SO_2NAA'$.

Irrespective of further substitutions, Het denotes, for example, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, particularly preferably benzo-1,3-dioxol-4- or 5-yl, benzofuran-3-, 4-, 5- or 6-yl, benzothiophen-3-, 4-, 5- or 6-yl, benzo-1,2,5-thiadiazol-5- or 6-yl, imidazo[1,2a]pyridin-2-, 3-, 4-, 5-, 6-, 7-yl, 5-phenyl-oxazol-3- or 4-yl, furan-2- or 3-yl, imidazol-4-yl, 5-phenyl-furan-2-, 3- or 4-yl.

The heterocyclic radicals may also be partially or fully hydrogenated.

Het can thus, for example, 2-, 3-, 5-, 6-, 7- or 8-3,4-dihydro-2H-benzo-1,4-oxazinyl, 2,3,-dihydrobenzo-1,4-dioxin-5- or 6-yl, further preferably 2,3-dihydrobenzofuran-5- or 6-yl, or 2,3-dihydro-2-oxofuranyl.

Het preferably denotes a mono- or bicyclic saturated, unsaturated or aromatic heterocycle having 1 to 4 N, O and/or S atoms, which may be mono-, di- or trisubstituted by A, and/or Hal.

Het particularly preferably denotes a bicyclic saturated, unsaturated or aromatic heterocycle having 1 to 3 N, O and/or S atoms, which may be mono- or disubstituted by A and/or Hal, where A preferably denotes methyl, ethyl, propyl, butyl, pentyl, hexyl, isopropyl or trifluoromethyl.

$Het^1$ preferably denotes a monocyclic saturated or aromatic heterocycle having 1 to 2 N and/or O atoms, which may be mono- or disubstituted by A, OH, OA, Hal, $SO_2A$ and/or =O (carbonyl oxygen).

In a further embodiment, $Het^1$ particularly preferably denotes piperidine, piperazine, pyrrolidine, morpholine, furan, tetrahydropyran, pyridine, pyrrole, indole, indazole, isoxazole or imidazole, each of which is unsubstituted or mono- or disubstituted by A, OH, OA, Hal, $SO_2A$ and/or =O (carbonyl oxygen), where A preferably denotes methyl, ethyl, propyl, butyl, pentyl, hexyl, isopropyl or trifluoromethyl, Hal preferably denotes F, Cl or Br, OA preferably denotes methoxy, ethoxy or propoxy, and A in $SO_2A$ is preferably methyl, ethyl, propyl or butyl.

Very particular preference is given to piperidine, piperazine, pyrrolidine, morpholine, furan, tetrahydropyran, tetrahydrofuran, indazole, isoxazole or imidazole, each of which is unsubstituted or mono- or disubstituted by A, OH, OA, Hal, $SO_2A$ and/or =O (carbonyl oxygen), where A preferably denotes methyl, ethyl, propyl, isopropyl, butyl or trifluoromethyl, Hal preferably denotes F or Cl, OA preferably denotes methoxy, ethoxy or propoxy, and A in $SO_2A$ is preferably methyl, ethyl, propyl or butyl.

Ar denotes phenyl which is monosubstituted by $SO_2NH_2$, $SO_2NA$ or $SO_2NAA'$, where $SO_2NH_2$ is particularly preferred.

The compounds of the formula I may have one or more chiral centres and therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds can be expressed by the following sub-formulae Ia to Im, which conform to the formula I and in which the radicals not designated in greater detail have the meaning indicated for the formula I, but in which in Ia $R^2$ denotes H, A, $AlkNH_2$, AlkNHA, AlkNAA', $AlkNHSO_2A$, AlkOH, AlkOA, AlkCyc, AlkCycAlkOH, AlkCycAlkOA, AlkCycAlkCOOA, AlkCycAlkCOOH, $AlkHet^1$, AlkOAlkOH, AlkOAlkOA, $AlkOAlkNH_2$, AlkOARNHA, AlkOAlkNAA', $AlkCHOH(CH_2)_nOH$, $AlkO(CH_2)_mHet^1$ or AlkAr and $R^3$ denotes H;

in Ib $R^2$ and $R^3$ together may also be an alkylene chain having 1 to 5 C atoms, in which one non-adjacent $CH_2$ group may be replaced by an N or O atom and/or in which 1 or 2 H atom may be replaced by A, OH, OA, $(CH_2)_nHet^1$, and/or $SO_2A$, in Ic Alk denotes methylene, ethylene, propylene, butylene, pentylene or hexylene;

in Id Cyc cyclopropane, cyclobutane, cyclopentane or cyclohexane, each of which may be unsubstituted or monosubstituted by OH or OA;

in Ie Het a mono- or bicyclic unsaturated and/or aromatic heterocycle having 1 to 3 N, O and/or S atoms, which may be mono-, di- or trisubstituted by A, Hal and/or Ar, in If Het benzofuranyl, benzothiophenyl, benzo-1,2,5-thiadiazolyl, indolyl, isoindolyl, 2,3,-dihydrobenzo-1,4-dioxinyl, benzo-1,3-dioxolyl, 2,3-dihydrobenzofuranyl, 2,3-dihydro-2-oxofuranyl, benzimidazolyl, indazolyl, imidazo[1,2-a]pyridinyl, benzothiazolyl, benzisothiazolyl, isoxazolyl, phenylisoxazolyl, (uranyl, phenylfuranyl, imidazolyl, each of which may be mono- or disubstituted by A and/or Hal;

in Ig Het indolyl, isoindolyl, benzimidazolyl, indazolyl, benzothiazolyl, benzisothiazolyl, 2,3,-dihydrobenzo-1,4-dioxinyl, benzo-1,3-dioxolyl, benzofuranyl, benzothiophenyl, benzo-1,2,5-thiadiazolyl, imidazo[1,2a]-pyridinyl, each of which may be mono- or disubstituted by A;

in Ih $Het^1$ a monocyclic saturated or unsaturated heterocycle having 1 to 3 N, O and/or S atoms, which may be mono-, di- or trisubstituted by A, Hal, $SO_2A$ and/or =O (carbonyl oxygen) or in Ii $Het^1$ a monocyclic saturated or unsaturated heterocycle having 1 to 2 N and/or O atoms, which may be mono- or disubstituted by A and/or =O (carbonyl oxygen)

in Ij $Het^1$ piperazinyl, morpholinyl, piperidinyl, pyrrolidinyl, tetrahydropyranyl, tetrahydrofuranyl, imidazolyl, each of which may be unsubstituted or mono- or disubstituted by A, and/or =O (carbonyl oxygen), in Ik Ar phenyl which is monosubstituted by $SO_2NH_2$, $SO_2NA$ or $SO_2NAA'$;

in Il A, A' unbranched or branched alkyl having 1-6 C atoms, in which 1-5 H atoms may be replaced by F and/or Cl, in Im $R^1$ denotes Het $R^2$ denotes H, A, $AlkNH_2$, AlkNHA, AlkNAA', $AlkNHSO_2A$, AlkOH, AlkOA, AlkCyc, AlkCycAlkOH, AlkCycAlkOA, AlkCycAlkCOOA, AlkCycAlkCOOH, $AlkHet^1$, AlkOAlkOH, AlkOAlkOA, $AlkOAlkNH_2$, AlkOAlkNHA, AlkOAlkNAA', $AlkCHOH(CH_2)_nOH$, $AlkO(CH_2)_mHet^1$ or AlkAr, $R^3$ denotes H, $R^2$ and $R^3$ together may also be an alkylene chain having 1 to 5 C atoms, in which one non-adjacent $CH_2$ group may be replaced by an N or O atom and/or in which 1 H atom may be replaced by A, OH, OA, $(CH_2)_nHet^1$, or $SO_2A$, Alk denotes methylene, ethylene, propylene, butylene, pentylene or hexylene, Cyc denotes cyclopropane, cyclobutane, cyclopentane or cyclohexane, each of which may be unsubstituted or monosubstituted by OH, Het denotes benzofuranyl, benzothiophenyl, benzo-1,2,5-thiadiazolyl, indolyl, isoindolyl, 2,3,-dihydrobenzo-1,4-dioxinyl, benzo-1,3-dioxolyl, 2,3-dihydrobenzofuranyl, 2,3-dihydro-2-oxofuranyl, benzimidazolyl, indazolyl, imidazo[1,2-a]pyridinyl, benzothiazolyl, benzisothiazolyl, isoxazolyl, phenylisoxazolyl, furanyl, phenylfuranyl, imidazolyl, each of which may be mono- or disubstituted by A and/or Hal, $Het^1$ denotes a monocyclic saturated heterocycle having 1 to 2 N and/or O atoms, which may be mono- or di-substituted by A and/or =O (carbonyl oxygen), Ar denotes phenyl which is monosubstituted by $SO_2NH_2$, $SO_2NA$ or $SO_2NAA'$, A, A' denote unbranched or branched alkyl having 1-6 C atoms, in which 1-5H atoms may be replaced by F and/or Cl, Hal denotes F, Cl, Br or I, m denotes 1, 2, 3, 4, n denotes 0, 1, 2, 3, 4 and pharmaceutically usable derivatives, solvates, salts, tautomers and stereoisomers thereof, including mixtures thereof in all ratios.

The compounds according to the invention and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions.

Use can also be made here of variants known per se which are not mentioned here in greater detail.

If desired, the starting materials can also be formed in situ by not isolating them from the reaction mixture, but instead immediately converting them further into the compounds according to the invention.

The starting compounds are generally known. If they are novel, however, they can be prepared by methods known per se.

Compounds of the formula I in which $R^2$ and $R^3$=H can preferably be obtained by reacting a compound of the formula II with a compound of the formula III.

The compounds of the formula II and III are generally known. If they are not known, they can be prepared by methods known per se.

In the compounds of the formula III, Z preferably denotes Cl, Br, I or a reactively modified OH group, such as alkylsulfonyloxy having 1-6 C atoms (preferably methylsulfonyloxy) or arylsulfonyloxy having 6-10 C atoms (preferably phenyl- or p-tolylsulfonyloxy). Z particularly preferably denotes Cl.

The reaction is carried out by methods which are known to the person skilled in the art.

The reaction is preferably carried out under basic conditions. Suitable bases are preferably alkali metal hydroxides, including potassium hydroxyide, sodium hydroxide and lithium hydroxide; alkaline earth metal hydroxyides, such as barium hydroxide and calcium hydroxide; alkali metal alkoxides, for example potassium ethoxide and sodium propoxide; and various organic bases, such as piperidine or diethanolamine.

The reaction is carried out in a suitable inert solvent.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The solvent is particularly preferably, for example, water and/or tetrahydrofuran.

In the reaction, firstly a compound of the formula IV is formed, which subsequently cyclised to give the compound of the formula I. The compound of the formula IV can be isolated as intermediate and used, for example, as starting compound for the preparation of compounds of the formula I in which at least one of the two radicals $R^2$, $R^3$ is ≠H.

Depending on the conditions used, the reaction time is between a few minutes and 14 days, the reaction temperature is between about −30° and 140°, normally between −10° and 130°, in particular between about 30° and about 125°.

Compounds of the formula I in which at least one of the two radicals $R^2$, $R^3$ is ≠H can preferably be obtained by firstly exchanging the free amino group in a compound of the formula IV with Hal, CSF CSF reacting the resultant compound of the formula V with a compound of the formula VI to give a compound of the formula VII, and subsequently cyclising the latter.

The reaction is preferably carried out in inert solvents; as described above, acetone, acetonitrile and/or ethanol are particularly preferred.

Depending on the conditions used, the reaction time is between a few minutes and 14 days, the reaction temperature is between about −30° and 140°, normally between −10° and 130°, in particular between about 30° and about 125°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formula I in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds of the formula I may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active compounds.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.1 mg to 3 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the human or animal, the precise condition that requires treatment, and its severity, the nature of the formulation and the method of administration, and is ultimately determined by the treating doctor or vet. However, an effective amount of a compound according to the invention for the treatment is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound of the formula I per se. It can be assumed that similar doses are suitable for the treatment of the other conditions mentioned above.

The invention relates to medicaments comprising at least one compound of the formula I and/or pharmaceutically usable derivatives, solvates and stereoisomers thereof, including mixtures thereof in all ratios, and optionally excipients and/or adjuvants and at least one further medicament active compound.

The invention furthermore relates to the use of compounds of the formula I and pharmaceutically usable derivatives, salts, solvates, tautomers and stereoisomers thereof, including mixtures thereof in all ratios, for the preparation of a medicament for the treatment and/or combating of cancer, tumour growth, metastatic growth, where the tumour is selected from the group of tumours of the squamous epithelium, of the bladder, of the stomach, of the kidneys, of head and neck, of the oesophagus, of the cervix, of the thyroid, of the intestine, of the liver, of the brain, of the prostate, of the urogenital tract, of the lymphatic system, of the stomach, of the larynx, of the lung, lung adenocarcinoma, small-cell lung carcinoma, pacreatic cancer, glioblastoma, colon carcinoma, breast carcinoma, tumour of the blood and immune system, acute myeloid leukaemia, chronic myeloid leukaemia, acute lymphatic leukaemia, chronic lymphatic leukaemia.

Further medicament active compounds are preferably chemotherapeutic agents, in particular those which inhibit angiogenesis and thus inhibit the growth and spread of tumour cells; preference is given here to VEGF receptor inhibitors, including robozymes and antisense which are directed to VEGF receptors, and angiostatin and endostatin.

Examples of antineoplastic agents which can be used in combination with the compounds according to the invention generally include alkylating agents, antimetabolites; epidophyllotoxin; an antineoplastic enzyme; a topoisomerase inhibitor; procarbazin; mitoxantron or platinum coordination complexes.

Antineoplastic agents are preferably selected from the following classes: anthracyclins, vinca medicaments, mitomycins, bleomycins, cytotoxic nucleosides, epothilones, discodermolides, pteridines, diynenes and podophyllotoxins.

Particular preference is given in the said classes to, for example, caminomycin, daunorubicin, aminopterin, methotrexate, methopterin, dichloromethotrexate, mitomycin C, porfiromycin, 5-fluorouracil, 5-fluorodeoxyuridine monophosphate, cytarabines, 5-azacytidine, thioguanine, azathioprines, adenosine, pentostatin, erythrohydroxynonyladenine, cladribines, 6-mercaptopurine, gemcitabine, cytosinarabinoside, podophyllotoxin or podophyllotoxin derivatives, such as, for example, etoposide, etoposide phosphate or teniposide, melphalan, vinblastine, vincristine, leurosidine, vindesine, leurosine and paclitaxel. Other preferred antineoplastic agents are selected from the group estramustine, carboplatin, cyclophosphamide, bleomycin, gemcitabine, ifosamide, melphalan, hexamethylmelamine, thiotepa, cytarabin, idatrexate, trimetrexate, dacarbazine, L-asparaginase, camptothecin, CPT-11, topotecan, arabinosylcytosine, bicalutamide, flutamide, leuprolide, pyridobenzoindole derivatives, interferons and interleukins.

Further medicament active compounds are preferably antibiotics. Preferred antibiotics are selected from the group dactinomycin, daunorubicin, idarubicin, epirubicin, mitoxantrone, bleomycin, plicamycin, mitomycin.

Further medicament active compounds are preferably enzyme inhibitors. Preferred enzyme inhibitors are selected from the group of the histone deacetylation inhibitors (for example suberoyl anilide hydroxamic acid [SAHA]) and the tyrosine kinase inhibitors (for example ZD 1839 [Iressa]).

Further medicament active compounds are preferably nuclear export inhibitors. Nuclear export inhibitors prevent the expression of biopolymers (for example RNA) from the cell nucleus. Preferred nuclear export inhibitors are selected from the group callystatin, leptomycin B, ratjadone.

Further medicament active compounds are preferably nuclear export inhibitors. Nuclear export inhibitors prevent the expression of biopolymers (for example RNA) from the cell nucleus. Preferred nuclear export inhibitors are selected from the group callystatin, leptomycin B, ratjadone.

Further medicament active compounds are preferably immunosuppressants. Preferred immunosuppressants are selected from the group rapamycin, CCI-779 (Wyeth), RAD001 (Novartis), AP23573 (Ariad Pharmaceuticals).

The invention also relates to a set (kit) consisting of separate packs of
(a) an effective amount of a compound of the formula I and/or pharmaceutically usable derivatives, solvates and stereoisomers thereof, including mixtures thereof in all ratios, and
(b) an effective amount of a further medicament active compound.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios,
and an effective amount of a further medicament active compound in dissolved or lyophilised form.

The compounds according to the invention and pharmaceutically usable derivatives, salts, solvates, tautomers and stereoisomers thereof, including mixtures thereof in all ratios, are suitable as pharmaceutical active compounds for mammals, in particular for humans, for the preparation of a medicament for the treatment and/or combating of cancer, tumour growth, metastatic growth, fibrosis, restenosis, HIV infection, Alzheimer's, atherosclerosis and/or for promoting wound healing.

The invention therefore relates to the use of compounds of the formula I and pharmaceutically usable derivatives, salts, solvates, tautomers and stereoisomers thereof, including mixtures thereof in all ratios, for the preparation of a medicament for the treatment and/or combating of cancer, tumour growth, metastatic growth, fibrosis, restenosis, HIV infection, Alzheimer's, atherosclerosis, and/or for promoting wound healing.

Particular preference is given to the use for the treatment of a disease, where the disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The invention also relates to the use of compounds according to Claim 1 and/or physiologically acceptable salts and solvates thereof for the preparation of a medicament for the treatment of solid tumours, where a therapeutically effective amount of a compound of the formula I is administered in combination with a compound from the group 1) oestrogen receptor modulator, 2) androgen receptor modulator, 3) retinoid receptor modulator, 4) cytotoxic agent, 5) antiproliferative agent, 6) prenyl-protein transferase inhibitor, 7) HMG-CoA reductase inhibitor, 8) HIV protease inhibitor, 9) reverse transcriptase inhibitor and 10) further angiogenesis inhibitors.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The present compounds are also suitable for combination with known anti-cancer agents. These known anticancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy. The synergistic effects of inhibiting VEGF in combination with radiotherapy have been described in the art (see WO 00/61186).

The invention therefore also relates to the use of compounds according to Claim 1 and/or physiologically acceptable salts and solvates thereof for the preparation of a medicament for the treatment of solid tumours, where a therapeutically effective amount of a compound of the formula I is administered in combination with radiotherapy and a compound from the group 1) oestrogen receptor modulator, 2) androgen receptor modulator, 3) retinoid receptor modulator, 4) cytotoxic agent, 5) antiproliferative agent, 6) prenyl-protein transferase inhibitor, 7) HMG-CoA reductase inhibitor, 8) HIV protease inhibitor, 9) reverse transcriptase inhibitor and 10) further angiogenesis inhibitors.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, loba-platin, satraplatin, profiromycin, cisplatin, irofulven, dexifosfamide, cisaminedichloro(2-methylpyridine)platinum, benzylguanine, glufosfamide, GPX100, (trans,trans,trans)bis-mu-(hexane-1,6-diamine)-mu-[diamineplatinum(II)]bis[diamine(chloro)platinum(II)]tetrachloride, diarisidinylspermine, arsenic trioxide, 1-(1'-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 742-(N-isopropylamino)ethyl'-(20S)camptothecin, BNP1350, BNPI1100, BN80915, BN80942, etoposide phosphate, teniposide, sobuzoxane, 2"-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]-acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo-(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Cellular Assay for the Testing of TGF-Beta Receptor I Kinase Inhibitors

As an example, the ability of the inhibitors to eliminate TGF-beta-mediated growth inhibition is tested.

Cells of the lung epithelial cell line Mv1Lu are sown in a defined cell density in a 96-well microtitre plate and cultivated over 16 hours under standard conditions. The medium is subsequently replaced with medium which comprises 0.5% of FCS and 1 ng/ml of TGF-beta, and the test substances are added in defined concentrations, generally in the form of dilution series with 5-fold steps. The concentration of the solvent DMSO is constant at 0.5%. After 48 hours, Crystal Violet staining of the cells is carried out. After extraction of the Crystal Violet from the fixed cells, the absorption is measured spectrophotometrically at 550 nm. It can be used as a quantitative measure of the adherent cells present and thus of the cell proliferation during the culture.

In-Vitro (Enzyme) Assay for the Determination of the Efficacy of Inhibitors of the Inhibition of TGF-Beta-Promoted Effects Vermittelten Wirkungen The kinase assay is carried out as 384-well flashplate assay. 31.2 nM of GST-ALK5, 439 nM of GST-SMAD2 and 3 mM of ATP (with 0.3 µCi of $^{33}$P-ATP/well) are incubated in a total volume of 35 µl (20 mM of HEPES, 10 mM of MgCl, 5 mM of MnCl, 1 mM of DTT, 0.1% of BSA, pH 7.4) without or with test substance (5-10 concentrations) at 30° C. for 45 min. The reaction is stopped using 25 µl of 200 mM EDTA solution, filtered with suction at room temperature after 30 min, and the wells are washed with 3 times 100 µl of 0.9% NaCl solution. Radioactivity is measured in the TopCount. The $IC_{50}$ values are calculated using RS1.

TABLE 1

Inhibition of TGF-beta

| Compound No. | $IC_{50}$ [mol/l] |
|---|---|
| "A30" | 6.3E-08 |
| "A53" | 2.4E-07 |
| "A16" | 2.9E-07 |
| "A41" | 1.8E-07 |

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$

FAB (fast atom bombardment) $(M+H)^+$

ESI (electrospray ionisation) $(M+H)^+$

APCI-MS (atmospheric pressure chemical ionisation-mass spectrometry) $(M+H)^+$.

Retention Time Rt [min]: Determination is Carried Out by HPLC

Column: Chromolith SpeedROD, 50×4.6 mm² (Order No. 1.51450.0001) from Merck

Gradient: 5.0 min, t=0 min, A:B=95:5, t=4.4 min: A:B=25:75, t=4.5 min to t=5.0 min: A:B=0:100

Flow rate: 3.00 ml/min

Eluent A: water+0.1% of TFA (trifluoroacetic acid),

Eluent B: acetonitrile+0.08% of TFA

Wavelength: 220 nm

LC-MS Conditions

Hewlett Packard HP 1100 series system with the following features: ion source: electrospray (positive mode); scan: 100-1000 m/e; fragmentation voltage: 60 V; gas temperature: 300° C., DAD: 220 nm.

Flow rate: 2.4 ml/min. The splitter used reduced the flow rate for the MS after the DAD to 0.75 ml/min.

Column: Chromolith SpeedROD RP-18e 50-4.6

Solvent LiChrosolv grade from Merck KGaA

Solvent A: H2O (0.01% of TEA)

Solvent B: ACN (0.008% of TFA)

Gradient:

20% of B→100% of B: 0 min to 2.8 min

100% of B: 2.8 min to 3.3 min

100% of B→20% of B: 3.3 min to 4 min

The retention times $R_f$[min] and $M+H^+$ data MW indicated in the following examples are the measurement results of the LC-MS measurements.

EXAMPLE 1

General reaction scheme for the preparation of compounds of the formula I in which $R^2$ and $R^3$ each denotes H:

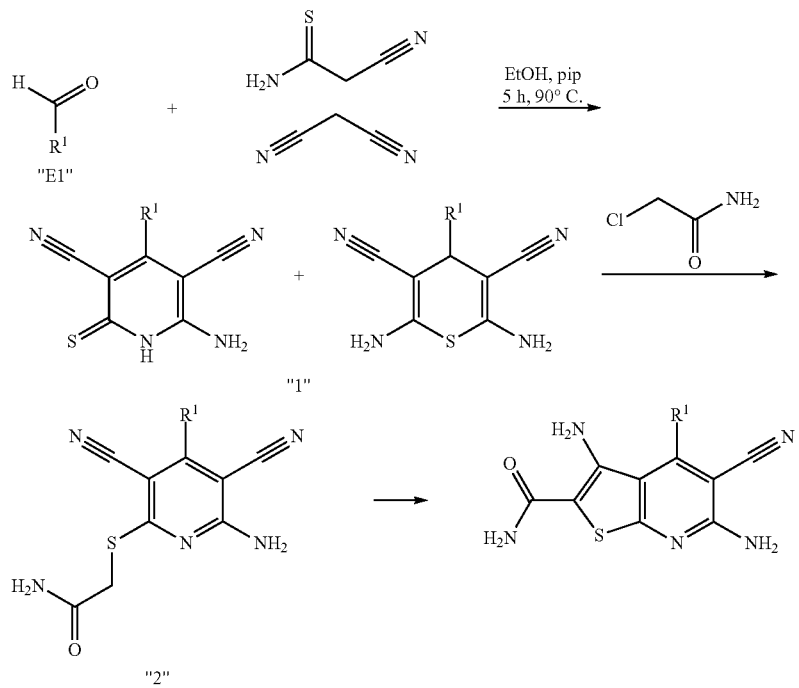

Preparation of 3,6-diamino-4-benzofuran-2-yl-5-cyan-othieno[2,3-b]pyridine-2-carboxamide ("A1"):

1.1 Firstly, 2.685 g of malononitrile and 4.196 g of cyanothio-acetamide are added to a solution of 6.0 g of benzofuran-2-carboxaldehyde ("E1") in 200 ml of ethanol. 203.2 µl of piperidine is then added, the resultant red-brown suspension is boiled at 90° C. for three hours and subsequently stirred at room temperature for 16 hours. The precipitated material (yellow and orange crystals) are separated off, washed with ethanol and dichloromethane and dried, giving 8.1530 g of a mixture of 6-amino-4-benzofuran-2-yl-2-thioxo-1,2-dihydropyridine-3,5-dicarbonitrile and 2,6-diamino-4-benzofuran-2-yl-2H-thiopyran-3,5-dicarbonitrile ("1"), which can be reacted further without purification.

1.2 One equivalent of aqueous potassium hydroxide solution and 320 mg of 2-chloroacetamide are added to a solution of 1.0 g of the mixture ("1") prepared in accordance with 1.1 in 15 ml of DMF. After one hour, one equivalent of potassium hydroxide solution is again added, and the mixture is stirred at room temperature for 16 hours. The precipitate is separated off, washed with water and dichloromethane and dried, giving 192 mg of white powder of 2-(6-amino-4-benzofuran-2-yl-3,5-dicyanopyridin-2-ylsulfanyl)acetamide ("2").

1.3 433 mg of "2" is dissolved in 10 ml of DMF, 483 µl of 10% aqueous potassium hydroxide solution KOH are added, and the mixture is stirred at room temperature for four hours, during which the solution changes to a deep-red colour. Flake ice is subsequently added, with an orange precipitate forming. The precipitate is separated off, washed with water and dried, giving 325.8 mg of orange-red powder of 3,6-diamino-4-benzofuran-2-yl-5-cyanothieno[2,3-b]pyridine-2-carboxamide ("A1").

$^{1}$H-NMR (500 MHz, DMSO-d$_{6}$) δ(ppm): 7.85 (1H, d), 7.77 (1H, d), 7.55 (1H, s), 7.5 (1H, t), 7.47 (2H, br, NH2), 7.42 (1H, t), 7.09 (2H, br, NH2), 6.19 (2H, br, NH2).

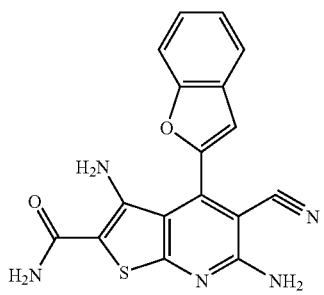

"A1"

The following are obtained analogously on exchange of "E1" with
- 4,5-dimethylfuran-2-carbaldehyde "A2",
- 5-methylfuran-2-carbaldehyde "A4",
- 5-ethylfuran-2-carbaldehyde "A5",
- benzofuran-2-carbaldehyde "A6",
- 5-vinylbenzo-1,2,5-thiadiazole "A7",
- 1-methyl-2-vinyl-1H-indole "A8",
- 5-methyl-2-vinylbenzofuran "A9",
- benzothiophene-2-carbaldehyde "A10",
- 2,3-dihydrobenzo-1,4-dioxin-6-carbaldehyde "A11",
- benzo-1,3-dioxole-5-carbaldehyde "A12",
- 1-methyl-1H-benzoimidazole-2-carbaldehyde "A13",
- 1-methyl-1H-indazole-3-carbaldehyde "A14",
- imidazo[1,2-a]pyridine-2-carbaldehyde "A15",
- benzothiazole-2-carbaldehyde "A16",
- benzo[b]thiophene-5-carbaldehyde "A17",
- 3-methyl-3H-imidazole-4-carbaldehyde "A18",
- 2-methyl-5-phenylfuran-3-carbaldehyde "A19",
- 5-methylisoxazole-3-carbaldehyde "20".

| No. | Structure and name | MW |
|---|---|---|
| "A2" | 3,6-Diamino-5-cyano-4-(4,5-dimethylfuran-2-yl)thieno[2,3-b]pyridine-2-carboxamide<br>HPLC-MS: [M + H] 328<br>1H-NMR (500 MHz, DMSO-d6) δ (ppm): 7.28 (2H, br, NH2), 6.98 (2H, br, NH2), 6.9 (1H, s, CH), 6.34 (2H, br, NH2), 2.33 (3H, s, CH3), 2.03 (3H, s, CH3) | 327.4 |
| "A4" | 3,6-Diamino-5-cyano-4-(5-methylfuran-2-yl)-thieno[2,3-b]pyridine-2-carboxamide<br>HPLC-MS: [M + H] 314<br>1H-NMR (500 MHz, DMSO-d6) δ (ppm): 7.31 (2H, br, NH2), 7.038 (2H, br, NH2), 6.98 (1H, d), 6.44 (1H, d), 6.28 (2H, br, NH2), 2.42 (3H, s, CH3) | 313.3 |
| "A5" | 3,6-Diamino-5-cyano-4-(5-ethylfuran-2-yl)-thieno[2,3-b] pyridine-2-carboxamide<br>HPLC-MS: [M + H] 328<br>1H-NMR (500 MHz, DMSO-d6) δ (ppm): 7.30 (2H, br, NH2), 7.03 (2H, br, NH2), 7.00 (1H, d), 6.46 (1H, d), 6.29 (2H, br, NH2), 2.78 (2H, q, CH2), 1.26 (3H, t, CH3) | 327.4 |

| No. | Structure and name | MW |
|---|---|---|
| "A6" | 3,6-Diamino-4-benzofuran-5-yl-5-cyanothieno-[2,3-b]pyridine-2-carboxamide<br>HPLC-MS: [M + H] 350<br>1H-NMR (500 MHz, DMSO-d6) δ (ppm): 8.15 (1H, d), 7.91 (1H, s), 7.80 (1H, m), 7.41 (1H, m), 7.28 (2H, br, NH2), 7.09 (1H, m), 6.94 (2H, br, NH2), 5.57 (2H, br, NH2) | 349.4 |
| "A7" | 3,6-Diamino-4-benzo-1,2,5-thiadiazol-5-yl-5-cyanothieno[2,3-b]pyridine-2-carboxamide<br>HPLC-MS: [M + H] 368<br>1H-NMR (500 MHz, DMSO-d6) δ (ppm): 8.35 (1H, s), 8,29 (1H, d), 7.77 (1H, d), 7.38 (2H, br, NH2), 6.98 (2H, br, NH2), 5.76 (2H, br, NH2) | 367.4 |
| "A8" | 3,6-Diamino-5-cyano-4-(1-methyl-1H-indol-2-yl)thieno[2,3-b]pyridine-2-carboxamide<br>HPLC-MS: [M + H] 363<br>1H-NMR (500 MHz, DMSO-d6) δ (ppm): 7.69 (1H, m), 7.61 (1H, m), 7.42 (2H, br, NH2), 7.31 (1H, m), 7.17 (1H, m), 7.01 (2H, br, NH2), 6.82 (1H, s), 5.66 (2H, br, NH2), 3.56 (3H, s, N—CH3) | 362.4 |
| "A9" | 3,6-Diamino-5-cyano-4-(5-methylbenzofuran-2-yl)thieno[2,3-b]pyridine-2-carboxamide<br>HPLC-MS: [M + H] 364<br>1H-NMR (500 MHz, DMSO-d6) δ (ppm): 7.63. (1H, s), 7.61 (1H, s), 7.46 (1H, s), 7.44 (2H, br, NH2), 7.29 (1H, m), 7.08 (2H, br, NH2), 6.17 (2H, br, NH2), 2.45 (3H, s, CH3) | 363.4 |
| "A10" | 3,6-Diamino-4-benzo[b]thiophen-2-yl-5-cyano-thieno[2,3-b]pyridine-2-carboxamide<br>HPLC-MS: [M + H] 366<br>1H-NMR (500 MHz, DMSO-d6) δ (ppm): 8.14 (1H, m), 8,01 (1H.m),7.76 (1H, s), 7.52 (2H, m), 7.42 (2H, br, NH2), 7.03 (2H, br, NH2), 5.92 (2H, br, NH2) | 365.4 |
| "A11" | 3,6-Diamino-5-cyano-4-(2,3-dihydrobenzo-1,4-dioxin-6-yl)thieno[2,3-b]pyridine-2-carboxamide<br>HPLC-MS: [M + H] 368 | 367.4 |

| No. | Structure and name | MW |
|---|---|---|
| "A12" | 3,6-Diamino-4-benzo-1,3-dioxol-5-yl-5-cyano-thieno[2,3-b]pyridine-2-carboxamide<br>HPLC-MS: [M + H] 354<br>1H-NMR (500 MHz, DMSO-d6) δ (ppm): 7.25 (2H, br, NH2), 7.10 (2H, m), 6.94 (2H, br, NH2), 6.93 (1H, m), 6.17 (1H, s), 6.14 (1H, s), 5.78 (2H, br, NH2) | 353.4 |
| "A13" | 3,6-Diamino-5-cyano-4-(1-methyl-1H-benzoimidazol-2-yl)thieno[2,3-b]pyridine-2-carboxamide<br>1H-NMR (500 MHz, DMSO-d6) δ (ppm): 7.82 (1H, d), 7.77 (1H, d), 7.60 (2H, br, NH2), 7.45 (1H, m), 7.39 (1H, m), 7.12 (2H, br, NH2), 5.98 (2H, br, NH2), 3.77 (3H, s, CH3) | 363.4 |
| "A14" | 3,6-Diamino-5-cyano-4-(1-methyl-1H-indazol-3-yl)thieno[2,3-b]pyridine-2-carboxamide<br>HPLC-MS: [M + H] 364 | 363.4 |
| "A15" | 3,6-Diamino-5-cyano-4-imidazo[1,2-a]pyridin-2-ylthieno[2,3-b]pyridine-2-carboxamide<br>HPLC-MS: [M + H] 350<br>1H-NMR (500 MHz, DMSO-d6) δ (ppm): 8.75 (1H, d), 8.54 (1H, s), 7.73 (1H, d), 7.45 (1H, m), 7.30 (2H, br, NH2), 7.18 (2H, br, NH2), 7.09 (1H, m), 6.96 (2H, br, NH2) | 349.4 |
| "A16" | 3,6-Diamino-4-benzothiazol-2-yl-5-cyanothieno-[2,3-b]pyridine-2-carboxamide<br>HPLC-MS: [M + H] 367<br>1H-NMR (500 MHz, DMSO-d6) δ (ppm): 8.33 (1H, d), 8.24 (1H, d), 7.69 (1H, t), 7.64 (1H, t), 7.54 (2H, br, NH2), 7.10 (2H, br, NH2), 5.99 (2H, br, NH2) | 366.4 |
| "A17" | 3,6-Diamino-4-benzo[b]thiophen-5-yl-5-cyano-thieno[2,3-b]pyridine-2-carboxamide<br>HPLC-MS: [M + H] 366<br>1H-NMR (500 MHz, DMSO-d6) δ (ppm): 8.25 (1H, d), 8.03 (1H, s), 7.93 (1H, d), 7.57 (1H, d), 7.45 (1H, d), 7.30 (2H, br, NH2), 6.94 (2H, br, NH2), 5.58 (2H, br, NH2) | 365.4 |

-continued

| No. | Structure and name | MW |
|---|---|---|
| "A18" | 3,6-Diamino-5-cyano-4-(3-methyl-3H-imidazol-4-yl)thieno[2,3-b]pyridine-2-carboxamide<br>HPLC-MS: [M + H] 314 | 313.3 |
| "A19" | 3,6-Diamino-5-cyano-4-(2-methyl-5-phenyl-furan-3-yl)thieno[2,3-b]pyridine-2-carboxamide | 389.4 |

-continued

| No. | Structure and name | MW |
|---|---|---|
| "A20" | 3,6-Diamino-5-cyano-4-(5-methylisoxazol-3-yl)-thieno[2,3-b]pyridine-2-carboxamide<br>HPLC-MS: [M + H] 315<br><br>1H-NMR (500 MHz, DMSO-d6) δ (ppm): 7.44 (2H, br, NH2), 7.05 (2H, br, NH2), 6.71 (1H, s), 6.14 (2H, br, NH2), 2.57 (3H, s, CH3) | 314.3 |

EXAMPLE 2

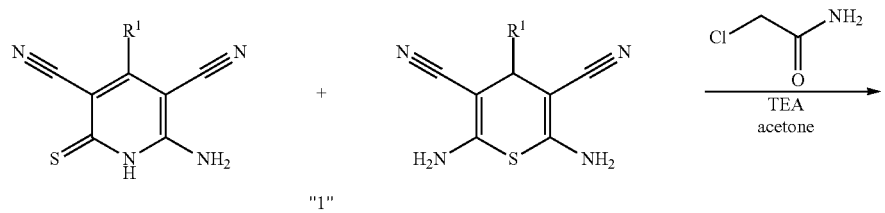

"1"

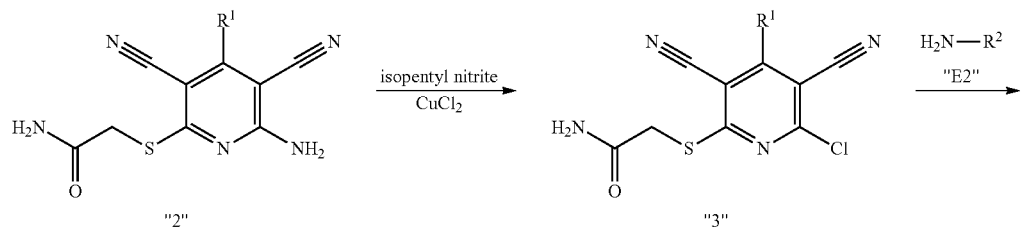

"2"     "3"

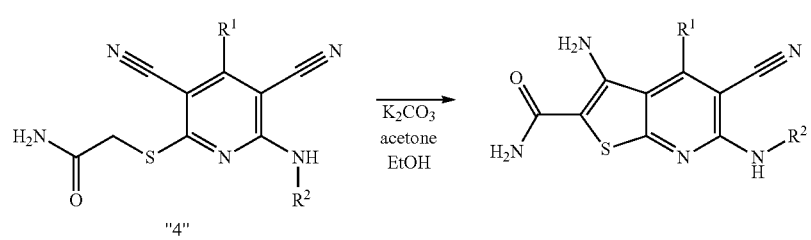

"4"

Preparation of 3-amino-4-benzofuran-2-yl-5-cyano-6-[3-(4-methylpiperazin-1-yl)propylamino]thieno[2,3-b]pyridine-2-carboxamide ("A30"):

2.1 Under an inert atmosphere, 8.14 g of ("2") are added to a solution of 3.97 g of copper(II) chloride and 4.96 ml of isopentyl nitrite 470 ml of dry acetonitrile. The resultant suspension is heated to 65° C. and stirred for 4 hours. The resultant red-brown solution is cooled to room temperature, transferred into 400 ml of hydrochloric acid (20% by weight) and extracted three times with 100 ml of ethyl acetate each time. The united organic phases are concentrated and transferred into ice-water. The resultant precipitate is separated off, washed with acetonitrile and water and dried, giving 3.1326 g of sand-coloured powder of 2-(4-benzofuran-2-yl-6-chloro-3,5-dicyanopyridin-2-yl-sulfanyl)acetamide ("3").

HPLC content: 95.8%

HPLC-MS: [M+H] 369

2.2 200 mg of 2-(4-benzofuran-2-yl-6-chloro-3,5-dicyanopyridin-2-ylsulfanyl)acetamide ("3") and 66 µl of 1-(3-aminopropyl)-4-methylpiperazine ("E2") in 2 ml of ethanol are stirred at room temperature for 16 hours. 66 µl of 1-(3-aminopropyl)-4-methylpiperazine and 2 ml of ethanol are subsequently added, and stirring is continued at room temperature for a further 12 hours. A precipitate is formed, which is separated off, washed with ethanol and dried, giving 236.1 mg of pale-yellow powder of 2-{4-benzofuran-2-yl-3,5-dicyano-6-[3-(4-methylpiperazin-1-yl)propylamino]pyridin-2-ylsulfanyl}acetamide ("4").

HPLC content: 93.2%

HPLC-MS: [M+H] 490

2.3 124 mg of potassium carbonate are added to a suspension of 236 mg of 2-{4-benzofuran-2-O-3,5-dicyano-6-[3-(4-methylpiperazin-1-yl)propylamino]pyridin-2-ylsulfanyl}acetamide ("4") in a mixture of 7 ml of anhydrous acetone and 7 ml of absolute ethanol, the mixture is heated to 65° C. and stirred for several hours. The mixture is subsequently cooled over 16 hours, the potassium carbonate is separated off, and the solvent is removed. The resultant residue is washed successively with ethanol, dichloromethane and ligroin, giving 112.6 mg of red powder of 3-amino-4-benzofuran-2-yl-5-cyano-6-[3-(4-methylpiperazin-1-yl)propylamino]thieno[2,3-b]pyridine-2-carboxamide ("A30").

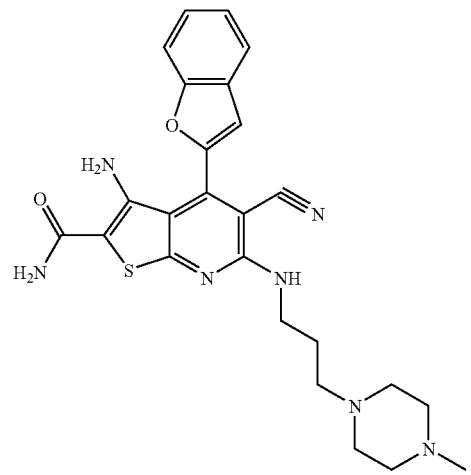

HPLC content: 95.5%

HPLC-MS: [M+H] 490

1H-NMR (500 MHz, DMSO-$d_6$) δ(ppm): 7.83 (1H, d), 7.73 (1H, d), 7.67 (1H, br, NH), 7.51 (1H, d), 7.48 (1H, m), 7.40 (1H, m), 7.05 (2H, br, NH2), 6.15 (2H, br, NH2), 3.61 (4H, m), 3.35 (4H, m), 2.95 (3H, s, CH3), 2.05 (4H, m), 1.09 (2H, m)

The following are obtained analogously on exchange of "E2" with
- butylamine "A31",
- 4-aminobutylamine "A32",
- morpholine "A33",
- 4-methylpiperazine "A34",
- 3-aminopropylpiperidine "A35",
- 3-morpholin-4-ylpropylamine "A36",
- 4-(4-methyl-3-oxopiperazin-1-yl)piperidine "A37",
- 2-(2-hydroxyethoxy)ethylamine "A38",
- 2-(4-methylpiperazin-1-yl)ethylamine "A39",
- 3-hydroxypyrrolidine "A40",
- 2,3-dihydroxypropylamine "A41",
- (3-hydroxycyclobutylmethyl)amine "A42",
- 4-ethanesulfonylpiperazine "A43",
- (tetrahydropyran-4-ylmethyl)amine "A44",
- (tetrahydrofuran-2-ylmethoxy)ethylamine "A45",
- 4-(4-methylpiperazin-1-yl)butylamine "A46",
- 6-(4-methylpiperazin-1-yl)hexylamine "A47",
- 2-methylaminoethylamine "A48",
- 4-pyrrolidin-1-ylpiperidine "A49",
- 3-imidazol-1-ylpropylamine "A50".

| No. | Structure and name | MW |
|---|---|---|
| "A31" | 3-Amino-4-benzofuran-2-yl-6-butylamino-5-cyanothieno[2,3-b]pyridine-2-carboxamide<br>HPLC-MS: [M + H] 406 | 405.5 |

-continued

| No. | Structure and name | MW |
|---|---|---|
| "A32" | 3-Amino-6-(4-aminobutylamino)-4-benzofuran-2-yl-5-cyanothieno[2,3-b]pyridine-2-carbox-amide<br>HPLC-MS: [M + H] 421 | 420.5 |
| "A33" | 3-Amino-4-benzofuran-2-yl-5-cyano-6-morpholin-4-ylthieno[2,3-b]pyridine-2-carboxamide<br>HPLC-MS: [M + H] 420<br>1H-NMR (500 MHz, DMSO-d6) δ (ppm): 7.84 (1H, d), 7.75 (1H, d), 7.57 (1H, s), 7.49 (1H, m), 7.40 (1H, m), 7.21 (2H, br, NH2), 6.23 (2H, br, NH2), 3.76 (4H, m), 3.68 (4H, m) | 419.5 |
| "A34" | 3-Amino-4-benzofuran-2-yl-5-cyano-6-(4-methylpiperazin-1-yl)thieno[2,3-b]pyridine-2-carboxamide<br>HPLC-MS: [M + H] 433 | 432.5 |

-continued
| No. | Structure and name | MW |
|---|---|---|
| "A35" | 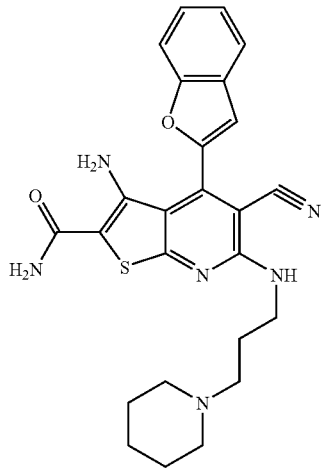<br>3-Amino-4-benzofuran-2-yl-5-cyano-6-(3-piperidin-1-ylpropylamino)thieno[2,3-b]pyridine-2-carboxamide<br>HPLC-MS: [M + H] 475 | 474.6 |
| "A36" | 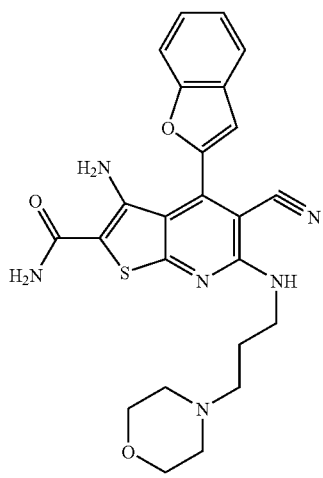<br>3-Amino-4-benzofuran-2-yl-5-cyano-6-(3-morpholin-4-ylpropylamino)thieno[2,3-b]pyridine-2-carboxamide<br>HPLC-MS: [M + H] 477 | 476.6 |

-continued
| No. | Structure and name | MW |
|---|---|---|
| "A37" | 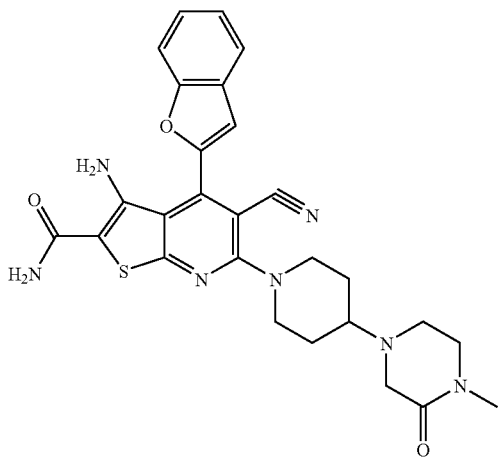<br>3-Amino-4-benzofuran-2-yl-5-cyano-6-[4-(4-methyl-3-oxopiperazin-1-yl)piperidin-1-yl]thieno-[2,3-b]pyridine-2-carboxamide<br>HPLC-MS: [M + H] 530 | 529.6 |
| "A38" | 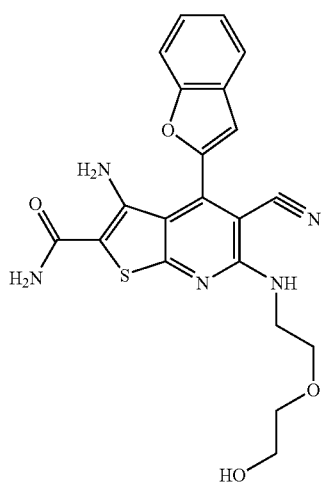<br>3-Amino-4-benzofuran-2-yl-5-cyano-6-[2-(2-hydroxyethoxy)ethylamino]thieno[2,3-b]pyridine-2-carboxamide<br>HPLC-MS: [M + H] 438<br>1H-NMR (500 MHz, DMSO-d6) δ (ppm): 7.83 (1H, d), 7.74 (1H, d), 7.54 (1H, d), 7.51 (1H, d), 7.48 (2H, m), 7.40 (1H, m), 7.08 (2H, br, NH2), 6.17 (2H, br, NH2), 4.6 (1H, br, OH), 3.63 (4H, m), 3.29 (4H, m) | 437.5 |

| No. | Structure and name | MW |
|---|---|---|
| "A39" | 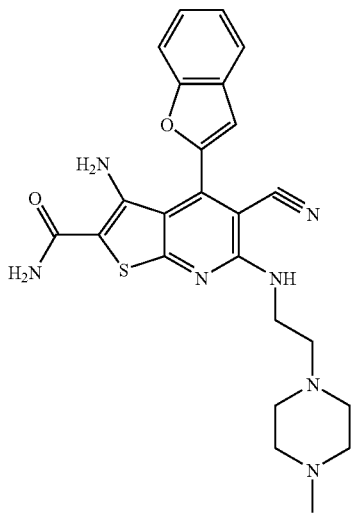
3-Amino-4-benzofuran-2-yl-5-cyano-6-[2-(4-methylpiperazin-1-yl)ethylamino]thieno[2,3-b]-pyridine-2-carboxamide
HPLC-MS: [M + H] 476
1H-NMR (500 MHz, DMSO-d6) δ (ppm): 7.84 (1H, d), 7.75 (1H, d), 7.55 (1H, s), 7.50 (1H, m), 7.40 (1H, m), 7.35 (1H, br, NH), 7.08 (2H, br, NH2), 6.19 (2H, br, NH2), 3.55 (4H, m), 2.55 (4H, m), 2.46 (2H, br), 2.31 (2H, br), 2.14 (3H, s, CH3) | 475.6 |
| "A40" | 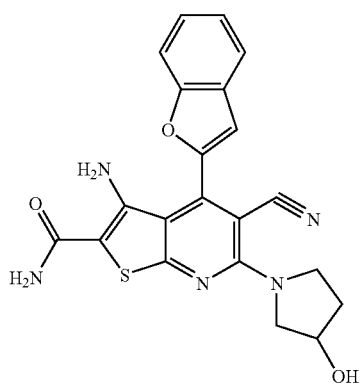
3-Amino-4-benzofuran-2-yl-5-cyano-6-(3-hydroxypyrrolidin-1-yl)thieno[2,3-b]pyridine-2-carboxamide
HPLC-MS: [M + H] 420 | 419.5 |

-continued

| No. | Structure and name | MW |
|---|---|---|
| "A41" | 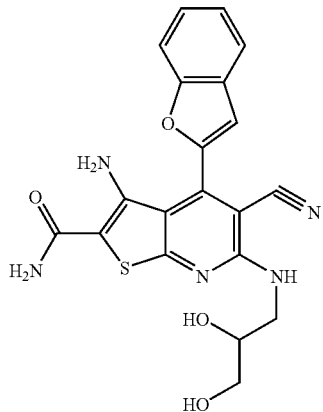<br>3-Amino-4-benzofuran-2-yl-5-cyano-6-(2,3-dihydroxypropylamino)thieno[2,3-b]pyridine-2-carboxamide<br>HPLC-MS: [M + H] 424<br>1H-NMR (500 MHz, DMSO-d6) δ (ppm): 7.84 (1H, d), 7.75 (1H, d), 7.55 (1H, br, NH), 7.48 (1H, m), 7.41 (1H, m), 7.17 (1H, m, OH), 7.09 (2H, br, NH2), 6.18 (2H, br, NH2), 4.93 (1H, m, OH), 4.66 (1H, m, OH), 3.76 (1H, m), 3.59 (1H, m), 3.41 (3H, m) | 423.5 |
| "A42" | 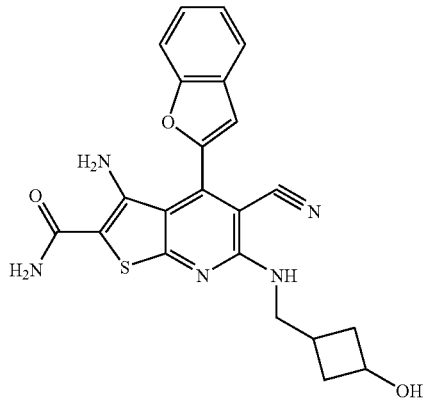<br>3-Amino-4-benzofuran-2-yl-5-cyano-6-[(3-hydroxycyclobutylmethyl)amino]thieno[2,3-b]-pyridine-2-carboxamide<br>HPLC-MS: [M + H] 434<br>1H-NMR (500 MHz, DMSO-d6) δ (ppm): 7.83 (1H, d), 7.75 (1H, d), 7.66 (1H, br, NH), 7.54 (1H, s), 7.48 (1H, t), 7.40 (1H, t), 7.09 (2H, br, NH2), 6.15 (2H, br, NH2), 5.0 (1H, br, OH), 3.88 (1H, m), 3.45 (2H, m), 2.24 (2H, m), 2.05 (1 H, m), 1.58 (2H, m) | 433.5 |

| No. | Structure and name | MW |
|---|---|---|
| "A43" | 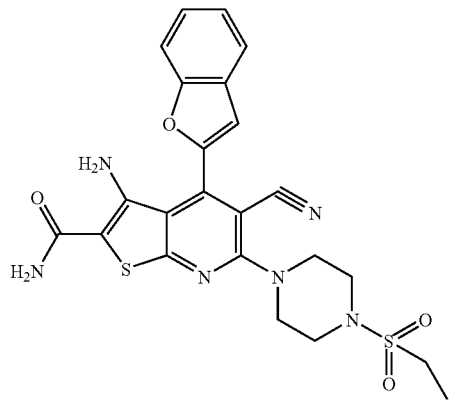<br>3-Amino-4-benzofuran-2-yl-5-cyano-6-(4-ethanesulfonylpiperazin-1-yl)thieno[2,3-b]-pyridine-2-carboxamide<br>HPLC-MS: [M + H] 511<br>1H-NMR (500 MHz, DMSO-d6) δ (ppm): 7.85 (1H, d), 7.76 (1H, d), 7.59 (1H, s), 7.50 (1H, t), 7.41 (1H, t), 7.26 (2H, br, NH2), 6.27 (2H, br, NH2), 3.75 (4H, m), 3.38 (4H, m), 3.13 (2H, q, CH2), 1.23 (3H, t, CH3) | 510.6 |
| "A44" | 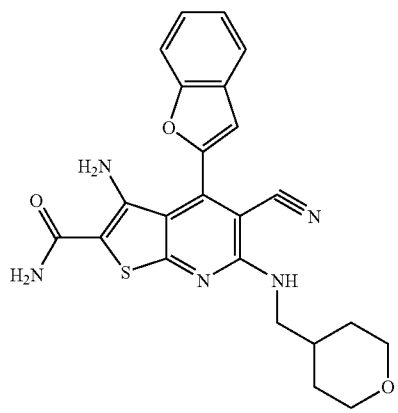<br>3-Amino-4-benzofuran-2-yl-5-cyano-6-[(tetrahydropyran-4-ylmethyl)amino]thieno-[2,3-b]pyridine-2-carboxamide<br>HPLC-MS: [M + H] 448<br>1H-NMR (500 MHz, DMSO-d6) δ (ppm): 7.83 (1H, d), 7.75 (1H, d), 7.66 (1H, br, NH), 7.54 (1H, s), 7.48 (1H, t), 7.40 (1H, t), 7.09 (2H, br, NH2), 6.16 (2H, br, NH2), 3.87 (2H, m), 3.40 (2H, m), 3.29 (2H, m), 1.98 (1H, m), 1.64 (2H, m), 1.27 (2H, m) | 447.5 |

-continued

| No. | Structure and name | MW |
|---|---|---|
| "A45" | 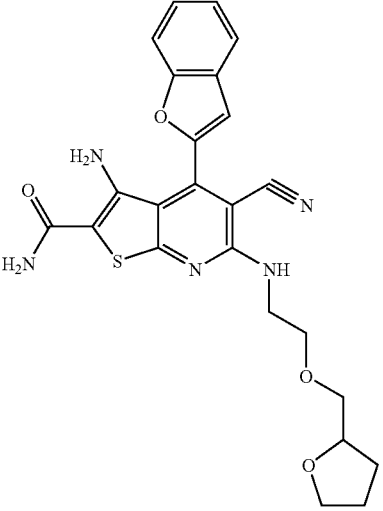<br>3-Amino-4-benzofuran-2-yl-5-cyano-6-[2-(tetrahydrofuran-2-ylmethoxy)ethylamino]-thieno[2,3-b]pyridine-2-carboxamide<br>HPLC-MS: [M + H] 478 | 477.5 |
| "A46" | 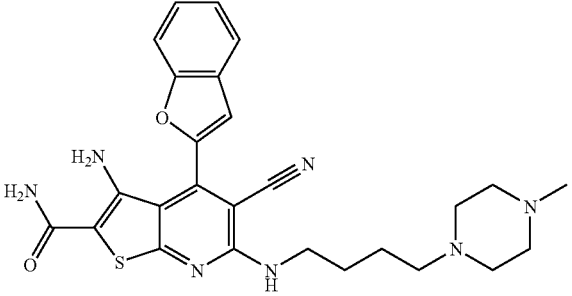<br>3-Amino-4-benzofuran-2-yl-5-cyano-6-[4-(4-methylpiperazin-1-yl)butylamino]thieno[2,3-b]-pyridine-2-carboxamide<br>HPLC-MS: [M + H] 504 | 503.6 |
| "A47" | 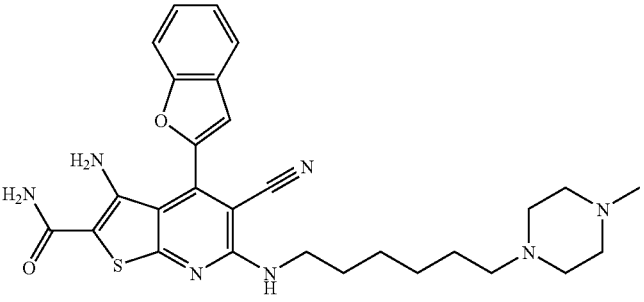<br>3-Amino-4-benzofuran-2-yl-5-cyano-6-[6-(4-methylpiperazin-1-yl)hexylamino]thieno[2,3-b]-pyridine-2-carboxamide<br>HPLC-MS: [M + H] 532 | 531.7 |

| No. | Structure and name | MW |
|---|---|---|
| "A48" | 3-Amino-4-benzofuran-2-yl-5-cyano-6-(2-methylaminoethylamino)thieno[2,3-b]pyridine-2-carboxamide<br>HPLC-MS: [M + H] 407 | 406.5 |
| "A49" | 3-Amino-4-benzofuran-2-yl-5-cyano-6-(4-pyrrolidin-1-ylpiperidin-1-yl)thieno[2,3-b]-pyridine-2-carboxamide<br>HPLC-MS: [M + H] 487 | 486.6 |
| "A50" | 3-Amino-4-benzofuran-2-yl-5-cyano-6-(3-imidazol-1-ylpropylamino)thieno[2,3-b]pyridine-2-carboxamide<br>HPLC-MS: [M + H] 459<br>1H-NMR (500 MHz, DMSO-d6) δ (ppm): 9.13 (1H, s), 7.85 (1H, d), 7.82 (1H, m), 7.76 (1H, d), 7.72 (1H, m), 7.70 (1H, m), 7.54 (1H, m), 7.50 (1H, m), 7.42 (1H, m), 7.10 (2H, br, NH2), 6.18 (2H, br, NH2), 4.30 (2H, m), 3.51 (2H, m), 2.20 (2H, m) | 457.5 |

EXAMPLE 3

If steps 1.1 and 1.2 according to Example 1 are carried out analogously with furan-2-carbaldehyde as "E1", 2-(6-amino-4-furan-2-yl-3,5-dicyanopyridin-2-ylsulfanyl)acetamide ("2a") is obtained. "2a" is subsequently reacted analogously to steps 2.1 to 2.3 according to Example 2, using 3-pyrrolidin-1-ylpropylamine as "E2" in step 2.2. 3-Amino-5-cyano-4-furan-2-yl-6-(3-pyrrolidin-1-ylpropylamino)thieno[2,3-b]pyridine-2-carboxamide "A51" is obtained.

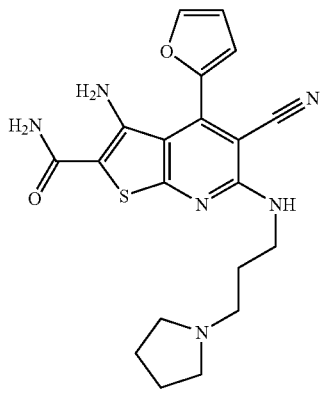

HPLC-MS: [M+H] 411

EXAMPLE 4

If steps 1.1 and 1.2 according to Example 1 are carried out analogously with 4,5-dimethylfuran-2-carbaldehyde as "E1", 2-(6-amino-4-(4,5-dimethylfuran-2-yl)-3,5-dicyanopyridin-2-ylsulfanyl)acetamide ("2b") is obtained.

"2b" is subsequently reacted analogously to steps 2.1 to 2.3 according to Example 2, using (methylpiperazin-1-yl)propylamine as "E2" in step 2.2. 3-Amino-5-cyano-4-(4,5-dimethylfuran-2-yl)-6-[3-(4-methylpiperazin-1-yl)propylamino]thieno[2,3-b]pyridine-2-carboxamide "A52" is obtained.

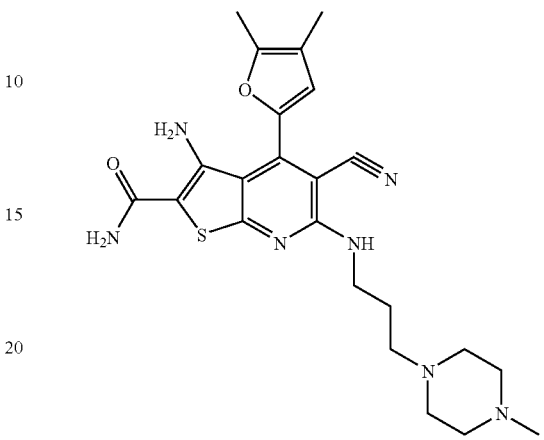

HPLC-MS: [M+H] 468
1H-NMR (500 MHz, DMSO-d6) δ(ppm): 7.5 (1H, br, NH), 7.0 (2H, br, NH2), 6.89 (1H, s), 6.3 (2H, br, NH2), 3.55 (4H, m), 3.3 (4H, m), 2.95 (3H, s, CH3), 2.35 (3H, s, CH3), 2.06 (3H, s, CH3), 2.03 (4H, m), 1.27 (2H, m)

The following are obtained analogously with "2b" and
4-ethanesulfonylpiperazine "A53",
(2-hydroxyethoxy)ethylamine "A54",
(4-sulfamoylphenyl)ethylamine "A55",
3-imidazol-1-ylpropylamine "A56",
3-methylaminopropylamine "A57",
3-hydroxypropylamine "A58",
piperidin-4-ylmethylamine "A58a"

| No. | Structure and name | MW |
|---|---|---|
| "A53" | 3-Amino-5-cyano-4-(4,5-dimethylfuran-2-yl)-6-(4-ethanesulfonylpiperazin-1-yl)thieno[2,3-b]-pyridine-2-carboxamide<br>HPLC-MS: [M + H] 489<br>1H-NMR (500 MHz, DMSO-d6) δ (ppm): 7.17 (2H, br, NH2), 7.0 (1H, s), 6.37 (2H, br, NH2), 3.68 (4H, m), 3.36 (4H, m), 3.13 (2H, q, CH2), 2.34 (3H, s, CH3), 2.05 (3H, s, CH3), 1.23 (3H, t, CH3) | 488.6 |

| No. | Structure and name | MW |
|---|---|---|
| "A54" | 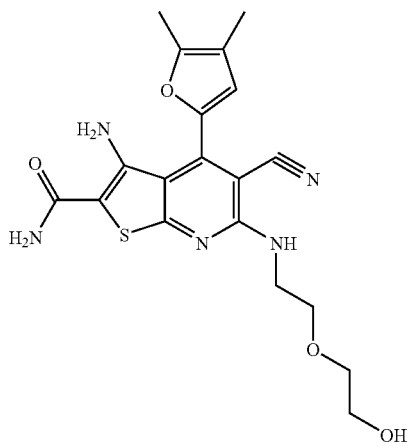<br>3-Amino-5-cyano-4-(4,5-dimethylfuran-2-yl)-6-[2-(2-hydroxyethoxy)ethylamino]thieno[2,3-b]-pyridine-2-carboxamide<br>HPLC-MS: [M + H] 416<br>1H-NMR (500 MHz, DMSO-d6) δ (ppm): 7.27 (1H, br, NH), 7.02 (2H, br, NH2), 6.90 (1H, s), 6.32 (2H, br, NH2), 4.56 (1H, m, OH), 3.59 (4H, m), 3.28 (4H, m), 2.33 (3H, s, CH3), 2.04 (3H, s, CH3) | 415.5 |
| "A55" | 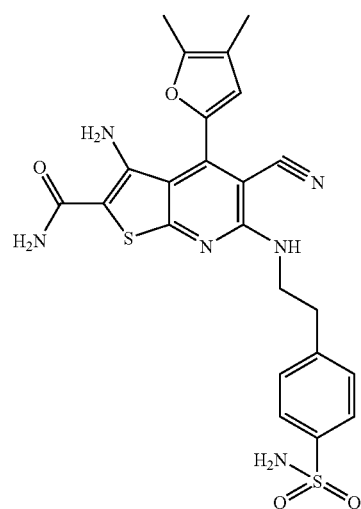<br>3-Amino-5-cyano-4-(4,5-dimethylfuran-2-yl)-6-[2-(4-sulfamoylphenyl)ethylamino]thieno[2,3-b]-pyridine-2-carboxamide<br>HPLC-MS: [M + H] 511 | 510.6 |

| No. | Structure and name | MW |
|---|---|---|
| "A56" | 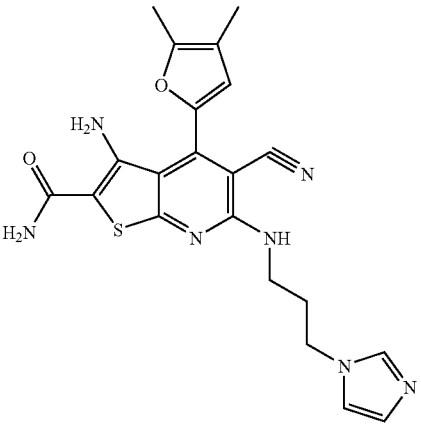<br>3-Amino-5-cyano-4-(4,5-dimethylfuran-2-yl)-6-(3-imidazol-1-ylpropylamino)thieno[2,3-b]pyridine-2-carboxamide<br>HPLC-MS: [M + H] 436<br>1H-NMR (500 MHz, DMSO-d6) δ (ppm): 7.63 (1H, s), 7.51 (1H, t), 7.18 (1H, s), 7.01 (2H, br, NH2), 6.89 (2H, br, NH + CH), 6.30 (2H, br, NH2), 4.03 (2H, m), 3.42 (2H, m), 2.33 (3H, s, CH3), 2.04 (5H, s + m), CH3 + CH2) | 435.5 |
| "A57" | 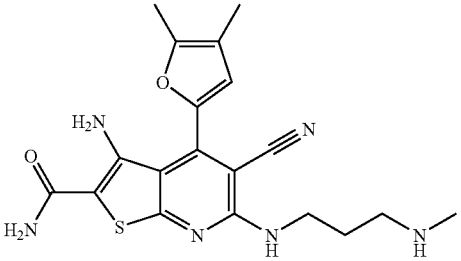<br>3-Amino-5-cyano-4-(4,5-dimethylfuran-2-yl)-6-(3-methylaminopropylamino)thieno[2,3-b]-pyridine-2-carboxamide<br>HPLC-MS: [M + H] 399<br>1H-NMR (500 MHz, DMSO-d6) δ (ppm): 8.50 (2H, br, NH2), 7.54 (1H, t, NH), 7.04 (2H, br, NH2), 6.91 (1H, s), 4.5 (1H, br, NH), 3.52 (2H, m), 2.94 (2H, m), 2.50 (3H, s, CH3), 2.33 (3H, s, CH3), 2.05 (3H, s, CH3), 1.91 (2H, m) | 398.5 |
| "A58" | 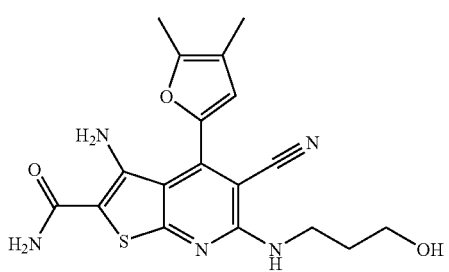<br>3-Amino-5-cyano-4-(4,5-dimethylfuran-2-yl)-6-(3-hydroxypropylamino)thieno[2,3-b]pyridine-2-carboxamide<br>HPLC-MS: [M + H] 386<br>1H-NMR (500 MHz, DMSO-d6) δ (ppm): 7.44 (1H, t, NH), 7.05 (2H, br, NH2), 6.91 (1H, s), 6.33 (2H, br, NH2), 4.60 (1H, t, OH), 3.50 (4H, m), 2.33 (3H, s), 2.03 (3H, s), 1.76 (2H, m) | 385.4 |

| No. | Structure and name | MW |
|---|---|---|
| "A58a" | 3-Amino-5-cyano-4-(4,5-dimethylfuran-2-yl)-6-[(piperidin-4-ylmethyl)amino]thieno[2,3-b]-pyridine-2-carboxamide | 424.5 |

EXAMPLE 5

If steps 1.1 and 1.2 according to Example 1 are carried out analogously with 5-methylfuran-2-carbaldehyde as "E1", 2-(6-amino-4-(5-methylfuran-2-yl)-3,5-dicyanopyridin-2-ylsulfanyl)acetamide ("2c") is obtained.

"2c" is subsequently reacted analogously to steps 2.1 to 2.3 according to Example 2, using 3-imidazol-1-ylpropylamine as "E2" in step 2.2. 3-Amino-5-cyano-6-(3-imidazol-1-yl-propylamino)-4-(5-methylfuran-2-yl)thieno[2,3-b]-pyridine-2-carboxamide "A59" is obtained.

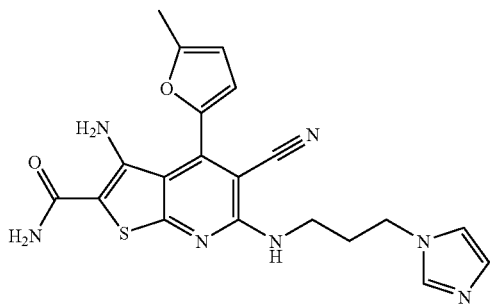

HPLC-MS: [M+H] 422

1H-NMR (500 MHz, DMSO-d6) δ(ppm): 7.65 (1H, s), 7.55 (1H, t, NH), 7.20 (1H, t), 7.04 (2H, br, NH2), 6.98 (1H, d), 6.90 (1H, t), 6.45 (1H, m), 6.27 (2H, br, NH2), 4.04 (2H, m), 3.44 (2H, m), 2.43 (3H, s, CH3), 2.06 (2H, m)

The following are obtained analogously with "2c" and 3-methylaminopropylamino "A60", 3-dimethylaminopropylamine "A61", 4-ethanesulfonylpiperazine "A62", 3-ethanesulfonylaminopropylamine "A63", 3-hydroxypropylamine "A64", 3-hydroxycyclobutylmethylamine "A65", methyl 2-aminomethylcyclopropanecarboxylate "A66", 4-hydroxybutylamine "A67", 3-methoxypropylamine "A68", 2-dimethylaminoethoxy)propylamine "A69",

| No. | Structure and name | MW |
|---|---|---|
| "A60" | 3-Amino-5-cyano-6-(3-methylamino-propylamino)-4-(5-methylfuran-2-yl)thieno-[2,3-b]pyridine-2-carboxamide<br>HPLC-MS: [M + H] 385<br>1H-NMR (500 MHz, DMSO-d6) δ (ppm): 8.64 (2H, br, NH2), 7.57 (1H, t, NH), 7.05 (2H, br, NH2), 6.99 (1H, d), 6.46 (1H, d), 4.6 (1H, br, NH), 3.52 (2H, m), 2.93 (2H, m), 2.49 (3H, s, CH3), 2.42 (3H, s, CH3), 1.93 (2H, m) | 384.5 |

| No. | Structure and name | MW |
|---|---|---|
| "A61" | 3-Amino-5-cyano-6-(3-dimethylamino-propylamino)-4-(5-methylfuran-2-yl)thieno-[2,3-b]pyridine-2-carboxamide<br>HPLC-MS: [M + H] 399<br>1H-NMR (500 MHz, DMSO-d6) δ (ppm): 8.15 (1H, t, NH), 7.01 (2H, br, NH2), 6.97 (1H, d), 6.44 (1H, d), 6.22 (2H, br, NH2), 3.50 (2H, m), 2.41 (3H, s, CH3), 2.37 (2H, m), 2.18 (6H, s, 2CH3), 1.73 (2H, m) | 398.5 |
| "A62" | 3-Amino-5-cyano-6-(4-ethanesulfonyl-piperazin-1-yl)-4-(5-methylfuran-2-yl)thieno-[2,3-b]pyridine-2-carboxamide<br>HPLC-MS: [M + H] 475<br>1H-NMR (500 MHz, DMSO-d6) δ (ppm): 7.19 (2H, br, NH2), 7.06 (1H, d), 6.47 (1H, d), 6.31 (2H, br, NH2), 3.69 (2H, m), 3.37 (2H, m), 3.12 (2H, q), 2.42 (3H, s), 1.23 (3H, t, CH3) | 474.6 |
| "A63" | 3-Amino-5-cyano-6-(3-ethanesulfonylamino-propylamino)-4-(5-methylfuran-2-yl)thieno-[2,3-b]pyridine-2-carboxamide<br>HPLC-MS: [M + H] 463<br>1H-NMR (500 MHz, DMSO-d6) δ (ppm): 7.41 (1H, t, NH), 7.01 (3H, br, NH2, NH), 6.96 (1H, d), 6.43 (1H, d), 6.24 (2H, br, NH2), 3.46 (2H, q), 2.97 (4H, m), 2.40 (3H, s), 1.77 (2H, m), 1.18 (3H, t, CH3) | 462.6 |

| No. | Structure and name | MW |
|---|---|---|
| "A64" | 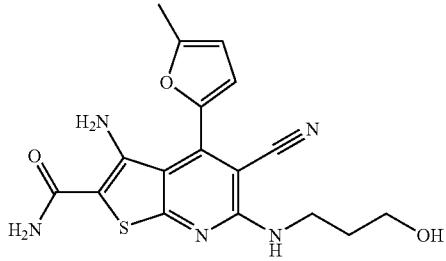<br>3-Amino-5-cyano-6-(3-hydroxypropylamino)-4-(5-methylfuran-2-yl)thieno[2,3-b]pyridine-2-carboxamide<br>HPLC-MS: [M + H] 372<br>1H-NMR (500 MHz, DMSO-d6) δ (ppm): 7.42 (1H, br, NH), 7.03 (2H, br, NH2), 6.98 (1H, d), 6.45 (1H, d), 6.26 (2H, br, NH2), 4.58 (1H, t, OH), 3.51 (4H, m), 2.42 (3H, s), 1.76 (2H, m) | 371.4 |
| "A65" | 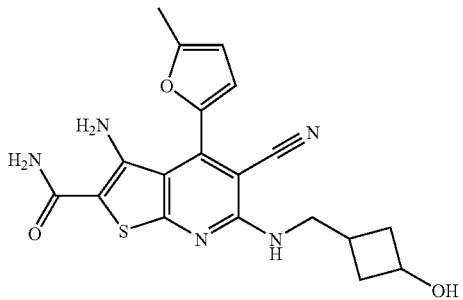<br>3-Amino-5-cyano-6-[(3-hydroxycyclobutylmethyl)-amino]-4-(5-methylfuran-2-yl)thieno[2,3-b]pyridine-2-carboxamide<br>HPLC-MS: [M + H] 398<br>1H-NMR (500 MHz, DMSO-d6) δ (ppm): 7.45 (1H, t, NH), 7.02 (2H, br, NH2), 6.97 (1H, d), 6.43 (1H, d), 6.24 (2H, br, NH2), 3.87 (1H, m), 3.44 (3H, m, CH2 + OH), 2.41 (3H, s), 2.24 (2H, m), 2.01 (1H, m), 1.57 (2H, m) | 397.5 |
| "A66" | 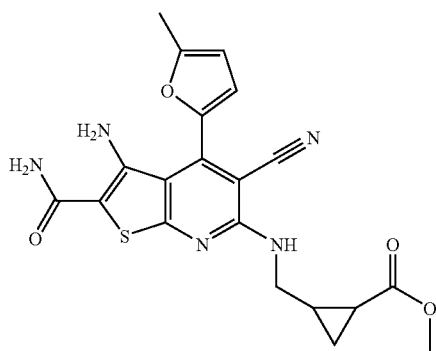<br>Methyl 2-{[3-amino-2-carbamoyl-5-cyano-4-(5-methylfuran-2-yl)thieno[2,3-b]pyridin-6-ylamino]methyl}cyclopropanecarboxylate<br>HPLC-MS: [M + H] 426 | 425.5 |

| No. | Structure and name | MW |
|---|---|---|
| "A67" | 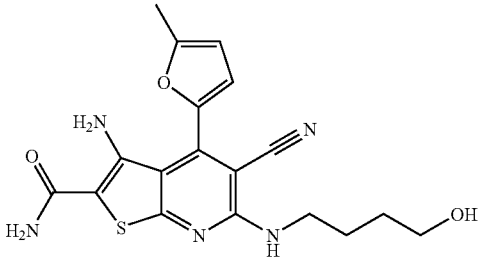<br>3-Amino-5-cyano-6-(4-hydroxybutylamino)-4-(5-methylfuran-2-yl)thieno[2,3-b]pyridine-2-carboxamide<br>HPLC-MS: [M + H] 386<br>1H-NMR (500 MHz, DMSO-d6) δ (ppm): 7.50 (1H, t, NH), 7.06 (2H, br, NH2), 6.99 (1H, d), 6.45 (1H, d), 6.27 (2H, br, NH2), 4.43 (1H, t, OH), 3.44 (4H, m), 2.43 (3H, s), 1.62 (2H, m), 1.48 (2H, m) | 385.4 |
| "A68" | 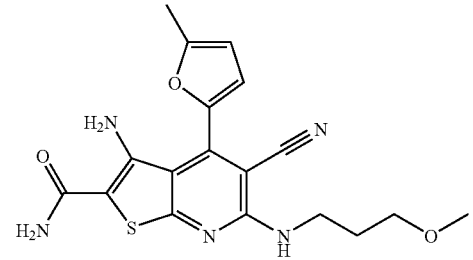<br>3-Amino-5-cyano-6-(3-methoxypropylamino)-4-(5-methylfuran-2-yl)thieno[2,3-b]pyridine-2-carboxamide<br>HPLC-MS: [M + H] 386<br>1H-NMR (500 MHz, DMSO-d6) δ (ppm): 7.44 (1H, br, NH), 7.04 (2H, br, NH2), 6.98 (1H, d), 6.45 (1H, d), 6.27 (2H, br, NH2), 3.49 (2H, m), 3.42 (2H, m), 3.27 (3H, s, CH3), 2.43 (3H, s, CH3), 1.84 (2H, m) | 385.4 |
| "A69" | 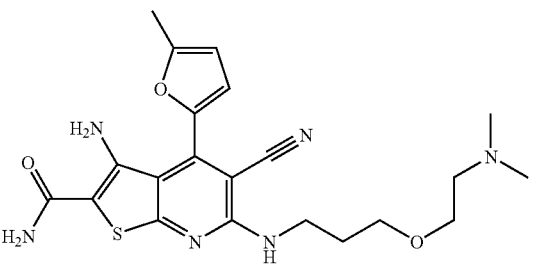<br>3-Amino-5-cyano-6-[3-(2-dimethylamino-ethoxy)propylamino]-4-(5-methylfuran-2-yl)-thieno[2,3-b]pyridine-2-carboxamide<br>HPLC-MS: [M + H] 443<br>1H-NMR (500 MHz, DMSO-d6) δ (ppm): 7.43 (1H, t, NH), 7.08 (2H, br, NH2), 6.99 (1H, d), 6.45 (1H, d), 6.28 (2H, br, NH2), 3.69 (2H, m), 3.53 (4H, m), 3.29 (2H, m), 2.81 (6H, s, NCH3), 2.42 (3H, s, CH3), 1.89 (2H, m) | 442.5 |

EXAMPLE 6

2-(6-Amino-4-benzofuran-2-yl-3,5-dicyanopyridin-2-yl-sulfanyl)acetamide ("2"), which is obtainable by steps 1.1 and 1.2 of Example 1, is reacted analogously to steps 2.1 to 2.3 of Example 2. On exchange of "E2" in step 2.2, the following are obtained with
- 3-aminopropylamine "A71",
- 3-ethanesulfonylaminopropylamine "A72",
- 3-hydroxypropylamine "A73",
- 3-methoxypropylamine "A74",
- 3-(2-dimethylaminoethoxy)propylamine "A75",
- 3-(4-dimethylaminobutoxy)propylamine "A76",
- 2-hydroxyethylamine "A77",
- 2-hydroxymethylcyclopropylmethylamine "A78",
- cis-2-hydroxymethylcyclopropylmethylamine "A79"
- piperidin-4-ylmethylamine "A80",

| No. | Structure and name | MW |
|---|---|---|
| "A70" | 3-Amino-4-benzofuran-2-yl-5-cyano-6-(3-methylaminopropylamino)thieno[2,3-b]-pyridine-2-carboxamide<br>HPLC-MS: [M + H] 421<br>1H-NMR (500 MHz, DMSO-d6) δ (ppm): 8.61 (2H, br, NH2), 7.84 (1H, d), 7.75 (1H, d), 7.71 (1H, t, NH), 7.54 (1H, s), 7.49 (1H, t), 7.41 (1H, t), 7.10 (2H, br, NH2), 4.5 (1H, br, NH), 3.55 (2H, m), 2.96 (2H, m), 2.50 (3H, s, CH3), 1.96 (2H, m) | 420.5 |
| "A71" | 3-Amino-6-(3-aminopropylamino)-4-benzofuran-2-yl)-5-cyanothieno[2,3-b]pyridine-2-carboxamide<br>HPLC-MS: [M + H] 407<br>1H-NMR (500 MHz, DMSO-d6) δ (ppm): 7.85 (1H, d), 7.81 (2H, br, NH2), 7.76 (1H, d), 7.70 (1H, t, NH), 7.55 (1H, s), 7.50 (1H, m), 7.42 (1H, m), 7.12 (2H, br, NH2), 3.8 (2H, br, NH2), 3.55 (2H, m), 2.89 (2H, m), 1.93 (2H, m) | 406.5 |

| No. | Structure and name | MW |
|---|---|---|
| "A72" | 3-Amino-4-benzofuran-2-yl-5-cyano-6-(3-ethanesulfonylaminopropylamino)thieno-[2,3-b]pyridine-2-carboxamide<br><br>HPLC-MS: [M + H] 499<br><br>1H-NMR (500 MHz, DMSO-d6) δ (ppm): 7.85 (1H, d), 7.77 (1H, d), 7.60 (1H, t, NH), 7.55 (1H, s), 7.50 (1H, t), 7.41 (1H, t), 7.10 (2H, br, NH2), 7.04 (1H, t, NH), 6.17 (2H, br, NH2), 3.52 (2H, q), 3.02 (4H, m), 1.82 (2H, m), 1.21 (3H, t, CH3) | 498.6 |
| "A73" | 3-Amino-4-benzofuran-2-yl-5-cyano-6-(3-hydroxypropylamino)thieno[2,3-b]pyridine-2-carboxamide<br><br>HPLC-MS: [M + H] 408 | 407.5 |

| No. | Structure and name | MW |
|---|---|---|
| "A74" | 3-Amino-4-benzofuran-2-yl-5-cyano-6-(3-methoxypropylamino)thieno[2,3-b]pyridine-2-carboxamide<br>HPLC-MS: [M + H] 422<br>1H-NMR (500 MHz, DMSO-d6) δ (ppm): 7.85 (1H, d), 7.77 (1H, d), 7.60 (1H, t, NH), 7.50 (1H, t), 7.41 (1H, t), 7.09 (2H, br, NH2), 6.17 (2H, br, NH2), 3.52 (2H, m), 3.43 (2H, m), 3.26 (3H, s, CH3), 1.86 (2H, m) | 421.5 |
| "A75" | 3-Amino-4-benzofuran-2-yl-5-cyano-6-[3-(2-dimethylaminoethoxy)propylamino]thieno-[2,3-b]pyridine-2-carboxamide<br>HPLC-MS: [M + H] 479<br>1H-NMR (500 MHz, DMSO-d6) δ (ppm): 7.84 (1H, d), 7.76 (1H, d), 7.56 (2H, m + s), 7.50 (1H, t), 7.41 (1H, t), 7.10 (2H, br, NH2), 6.18 (2H, br, NH2), 3.71 (2H, m), 3.55 (4H, m), 3.30 (2H, m), 2.81 (6H, s, NCH3), 1.91 (2H, m) | 478.6 |
| "A76" | 3-Amino-4-benzofuran-2-yl-5-cyano-6-[3-(4-dimethylaminobutoxy)propylamino]thieno-[2,3-b]pyridine-2-carboxamide<br>HPLC-MS: [M + H] 507<br>1H-NMR (500 MHz, DMSO-d6) δ (ppm): 7.84 (1H, d), 7.75 (1H, d), 7.53 (2H, br + s), 7.48 (1H, t), 7.40 (1H, t), 7.07 (2H, br, NH2), 6.16 (2H, br, NH2), 3.53 (2H, m), 3.46 (2H, m), 3.37 (2H, m), 2.16 (2H, m), 2.07 (6H, s, NCH3), 1.85 (2H, m), 1.49 (2H, m), 1.41 (2H, m) | 506.6 |

-continued

| No. | Structure and name | MW |
|---|---|---|
| "A77" | 3-Amino-4-benzofuran-2-yl-5-cyano-6-(2-hydroxyethylamino)thieno[2,3-b]pyridine-2-carboxamide<br>HPLC-MS: [M + H] 394 | 393.4 |
| "A78" | 3-Amino-4-benzofuran-2-yl-5-cyano-6-[trans-(2-hydroxymethylcyclopropylmethyl)amino]-thieno[2,3-b]pyridine-2-carboxamide<br>HPLC-MS: [M + H] 434<br>1H-NMR (500 MHz, DMSO-d6) δ (ppm): 7.85 (1H, d), 7.76 (1H, d), 7.65 (1H, t, NH), 7.56 (1H, s), 7.50 (1H, t), 7.41 (1H, t), 7.11 (2H, br, NH2), 6.17 (2H, br, NH2), 4.48 (1H, t, OH), 3.33 (3H, m), 3.18 (1H, m), 1.04 (1H, m), 0.96 (1H, m), 0.46 (1H, m), 0.35 (1H, m) | 433.5 |
| "A79" | 3-Amino-4-benzofuran-2-yl-5-cyano-6-[cis-(2-hydroxymethylcyclopropylmethyl)amino]-thieno[2,3-b]pyridine-2-carboxamide | 433.5 |

EXAMPLE 7

If Example 1 is carried out analogously, the following are obtained on exchange of "E1" with 5-(4-fluorophenyl)isoxazole-3-carbaldehyde "A80",
benzo[b]thiophene-3-carbaldehyde "A81".

| No. | Structure and name | MW |
|---|---|---|
| "A80" | 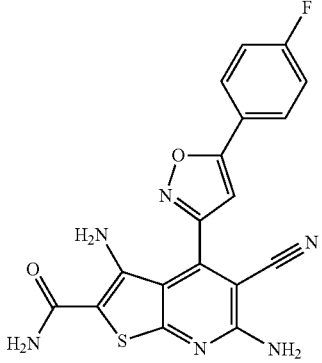<br>3,6-Diamino-5-cyano-4-[5-(4-fluorophenyl)-isoxazol-3-yl]thieno[2,3-b]pyridine-2-carboxamide<br>1H-NMR (500 MHz, DMSO-d6) δ (ppm): 8.05 (2H, m), 7.53 (2H, br, NH2), 7.48 (3H, m), 7.09 (2H, br, NH2), 6.18 (2H, br, NH2) | 394.4 |
| "A81" | 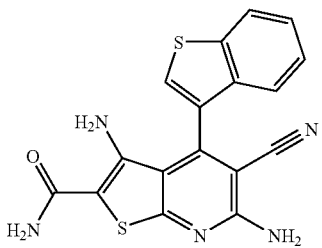<br>3,6-Diamino-4-benzo[b]thiophen-3-yl-5-cyano-thieno[2,3-b]pyridine-2-carboxamide<br>HPLC-MS: [M + H] 366 | 365.4 |

The following examples relate to medicaments:

EXAMPLE A

Injection Vials

A solution of 100 g of an active compound according to the invention and g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

EXAMPLE B

Suppositories

A mixture of 20 g of an active compound according to the invention with 100 g of soya lecithin and 1400 g of cocoa butter is melted, poured into moulds and allowed to cool. Each suppository contains 20 mg of active compound.

EXAMPLE C

Solution

A solution is prepared from 1 g of an active compound according to the invention, 9.38 g of $NaH_2PO_4 \cdot 2 H_2O$, 28.48 g of $Na_2HPO_4 \cdot 12 H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active compound according to the invention are mixed with 99.5 g of Vaseline under aseptic conditions.

EXAMPLE E

Tablets

A mixture of 1 kg of active compound, 4 kg of lactose, 1.2 kg of potato starch, 0.2 kg of talc and 0.1 kg of magnesium stearate is pressed in a conventional manner to give tablets in such a way that each tablet contains 10 mg of active compound.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of an active compound according to the invention are introduced into hard gelatine capsules in a conventional manner in such a way that each capsule contains 20 mg of the active compound.

EXAMPLE H

Ampoules

A solution of 1 kg of active compound according to the invention in 60 l of bidistilled water is sterile filtered, transferred into ampoules, lyophilised under sterile conditions and sealed under sterile conditions. Each ampoule contains 10 mg of active compound.

The invention claimed is:
1. A compound of the formula I

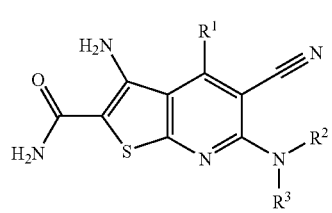

in which
$R^1$ denotes Het
$R^2$, $R^3$ each, independently of one another, denote H, A, $AlkNH_2$, AlkNHA, AlkNAA', $AlkNHSO_2A$, AlkOH, AlkOA, AlkCyc, AlkCycAlkOH, AlkCycAlkOA, AlkCycAlkCOOA, AlkCycAlkCOOH, AlkHet¹, AlkO-AlkOH, AlkOAlkOA, AlkOAlkNH₂, AlkOAlkNHA, AlkOAlkNAA', AlkCHOH(CH₂)$_n$OH, AlkO(CH₂)$_m$Het¹ or AlkAr, where one of the substituents $R^2$ and $R^3$ is not H, $R^2$ and $R^3$ together may also be an alkylene chain having 1 to 6 C atoms, in which one or two non-adjacent CH₂ groups may be replaced by N and/or O atoms and/or in which 1 to 6 H atoms may be replaced by A, OH, OA, (CH₂)$_n$Het¹, SO₂A and/or Hal, Alk denotes alkylene having 1 to 6 C atoms, in which 1 to 4 H atoms may be replaced by F, Cl and/or Br, Cyc denotes cycloalkyl having 3 to 7 C atoms, in which 1 to 4 H atoms may be replaced by A, Hal, OH and/or OA, Het denotes a benzofuranyl group, which may be mono- or disubstituted by A and/or Hal, Het¹ denotes a monocyclic saturated, unsaturated or aromatic heterocycle having 1 to 4 N, O and/or S atoms, which may be mono-, di- or trisubstituted by A, OH, OA, Hal, SO₂A and/or =O (carbonyl oxygen), Ar denotes phenyl which is unsubstituted or mono-, di- or trisubstituted by A, OH, OA, Hal, SO₂NH₂, SO₂NA and/or SO₂NAA', A, A' each, independently of one another, denote unbranched or branched alkyl having 1-10 C atoms, in which 1-5 H atoms may be replaced by F, Cl and/or Br, Hal denotes F, Cl, Br or I, m denotes 1, 2, 3, 4, n denotes 0, 1, 2, 3, 4, or a pharmaceutically usable salt, mono- or di-hydrate, alcoholate, tautomer or stereoisomer thereof, including mixtures thereof in all ratios.

2. A compound according to claim 1 in which $R^2$ denotes H, A, AlkNH₂, AlkNHA, AlkNAA', AlkNHSO₂A, AlkOH, AlkOA, AlkCyc, AlkCycAlkOH, AlkCycAlkOA, AlkCycAlkCOOA, AlkCycAlkCOOH, AlkHet¹, AlkOAlkOH, AlkOAlkOA, AlkOAlkNH₂, AlkOAlkNHA, AlkOAlkNAA', AlkCHOH(CH₂)$_n$OH, AlkO(CH₂)$_m$Het¹ or AlkAr and $R^3$ denotes H and or a pharmaceutically usable salt, mono- or di-hydrate, alcoholate, tautomer or stereoisomer thereof, including mixtures thereof in all ratios.

3. A compound according to claim 1 in which $R^2$ and $R^3$ together may also be an alkylene chain having 1 to 5 C atoms, in which one non-adjacent CH₂ group may be replaced by an N or O atom and/or in which 1 or 2 H atoms may be replaced by A, OH, OA, (CH₂)$_n$Het¹, and/or SO₂A, or a pharmaceutically usable salt, mono- or di-hydrate, alcoholate, tautomer or stereoisomer thereof, including mixtures thereof in all ratios.

4. A compound according to claim 1 in which

Het denotes a mono- or bicyclic unsaturated and/or aromatic heterocycle having 1 to 3 N, O and/or S atoms, which may be mono-, di- or trisubstituted by A, Hal and/or Ar, or a pharmaceutically usable salt, mono- or di-hydrate, alcoholate, tautomer or stereoisomer thereof, including mixtures thereof in all ratios.

5. A compound according to claim 1 in which

Het¹ a monocyclic saturated or unsaturated heterocycle having 1 to 3 N, O and/or S atoms, which may be mono-, di- or trisubstituted by A, Hal, SO₂A and/or =O(carbonyl oxygen), or a pharmaceutically usable salt, mono- or di-hydrate, alcoholate, tautomer or stereoisomer thereof, including mixtures thereof in all ratios.

6. A compound according to claim 1 in which

Ar denotes phenyl which is monosubstituted by SO₂NH₂, SO₂NA or SO₂NAA' or a pharmaceutically usable salt, mono- or di-hydrate, alcoholate, tautomer or stereoisomer thereof, including mixtures thereof in all ratios.

7. The compound:
3,6-diamino-5-cyano-4-(5-methylfuran-2-yl)thieno[2,3-b]pyridine-2-carboxamide, or a pharmaceutically usable salt, mono- or di-hydrate, alcoholate, tautomer or stereoisomer thereof, including mixtures thereof in all ratios.

8. Process for the preparation of a compound of the formula I according to claim 1 or a pharmaceutically usable salt, mono- or di-hydrate, alcoholate, tautomer or stereoisomer thereof, including mixtures thereof in all ratios, comprising:

a) for the preparation of a compound of the formula I in which $R^2$, $R^3$ =H, reacting a compound of the formula II

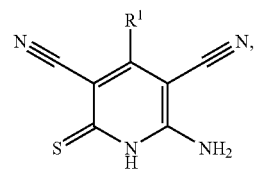

II in which $R^1$ has the meaning indicated in claim 1,
with a compound of the formula III

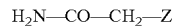

H₂N—CO—CH₂—Z    III in which

Z denotes Cl, Br, I or a free or reactive functionally modified OH group,
to give a compound of the formula IV

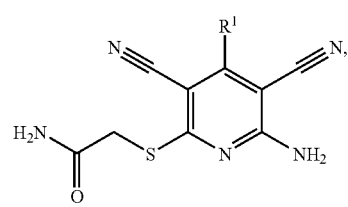

IV in which $R^1$ has the meaning indicated in claim 1,
and subsequently cyclizing the resultant compound of the formula IV to give the compound of the formula I, or b) for the preparation of the compound of the formula I in which at least one of the two radicals $R^2$, $R^3$ is ≠H,
replacing the free amino group in a compound of the formula IV by Hal, giving a compound of the formula V

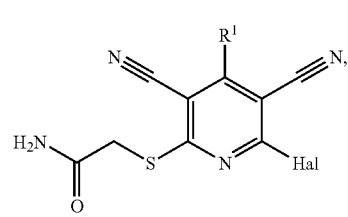

V in which $R^1$ has the meaning indicated in claim 1, then reacting the compound of the formula V with a compound of the formula VI

   VI in which $R^2$ and $R^3$ have the meanings indicated in claim 1, but at least one of the two radicals $R^2$, $R^3$ is ≠H, to give a compound of the formula VII

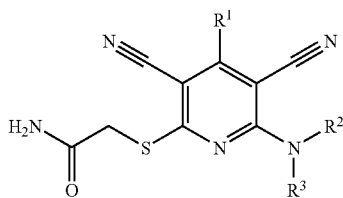   VII in which $R^1$, $R^2$, $R^3$ have the meanings indicated in claim 1, but at least one of the two radicals $R^2$, $R^3$ is ≠H, and subsequently cyclizing the resultant compound of the formula VII to give the compound of the formula I, and/or p1 c) converting a base or acid of the formula I into one of its salts.

9. A composition comprising at least one compound according to claim 1 or a pharmaceutically usable salt, mono- or di-hydrate, alcoholate, tautomer or stereoisomer thereof, including mixtures thereof in all ratios, and at least one excipient and/or adjuvant.

10. A composition comprising, as a medicament, at least one compound according to claim 1 or a pharmaceutically usable salt, mono- or di-hydrate, alcoholate, tautomer or stereoisomer thereof, including mixtures thereof in all ratios, and at least one further medicament active compound.

11. Set (kit) consisting of separate packs of
   (a) as a medicament, an effective amount of a compound of the according to claim 1 or a pharmaceutically usable salt, mono- or di-hydrate, alcoholate, tautomer or stereoisomer thereof, including mixtures thereof in all ratios, and
   (b) an effective amount of a further medicament active compound.

* * * * *